United States Patent
Ni et al.

(10) Patent No.: US 6,949,358 B1
(45) Date of Patent: Sep. 27, 2005

(54) HUMAN TUMOR NECROSIS FACTOR RECEPTOR TR9

(75) Inventors: Jian Ni, Rockville, MD (US); Guo-Liang Yu, San Mateo, CA (US); Ping Fan, Gaithersburg, MD (US); Reiner L. Gentz, Silver Spring, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 715 days.

(21) Appl. No.: 09/095,094

(22) Filed: Jun. 10, 1998

Related U.S. Application Data

(60) Provisional application No. 60/052,991, filed on Jun. 11, 1997.

(51) Int. Cl.[7] ........................... C12N 15/12; C07H 21/04
(52) U.S. Cl. ..................... 435/69.1; 536/23.5; 530/350; 435/320.1; 435/252.3; 435/325
(58) Field of Search ....................... 530/350; 536/23.5; 435/320.1, 252.3, 69.1, 6

(56) References Cited

U.S. PATENT DOCUMENTS

| | | | |
|---|---|---|---|
| 5,563,039 A | 10/1996 | Goeddel et al. | |
| 5,856,161 A | 1/1999 | Aggarwal et al. | |
| 6,013,476 A | 1/2000 | Deen et al. | |

FOREIGN PATENT DOCUMENTS

| | | |
|---|---|---|
| EP | 0 869 179 | 10/1998 |
| WO | 98/45437 | 10/1998 |
| WO | 98/56892 | 12/1998 |
| WO | 99/11790 | 3/1999 |
| WO | 99/15663 | 4/1999 |
| WO | 99/31128 | 6/1999 |
| WO | 99/46281 | 9/1999 |

OTHER PUBLICATIONS

Dietrich, F. S., Accession No.: S50578, EMBL Data Library, the sequence of *S. cerevisiae* lambda clone 3612 and cosmid 9794, superfamily protein–tyrosine–phosphatase homology, Dec. 1994.*

GenBank Accession No. AAC34583 (Sep. 5, 1998).
GenBank Accession No. AF068868 (Sep. 5, 1998).
GenBank Accession No. AL096801 (Nov. 29, 1999).
GenBank Accession No. AA156356 (Dec. 11, 1996).
GenBank Accession No. N49208 (Feb. 14, 1996).
GenBank Accession No. AA351536 (Apr. 21, 1997).
GenBank Accession No. AA155873 (Dec. 11, 1996).
GenBank Accession No. D59902 (Aug. 28, 1995).
GenBank Accession No. H41872 (Jul. 31, 1995).
GenBank Accession No. AA357231 (Apr. 21, 1997).
GenBank Accession No. H41873 (Jul. 31, 1995).
GenBank Accession No. T17352 (Feb. 14, 1997).
GenBank Accession No. AA374471 (Apr. 21, 1997).

International Search Report mailed on Aug. 28, 2000, in connection with a copending International Application.

Pan et al., *Identification and functional characterization of DR6, a novel death domain–containing TNF receptor*, FEBS Letters, 431:351–356 (1998).

Yoshimatsu et al., *Control of Gene Expression by Artificial Introns in Saccharomyces cerevisiae*, Science, 244:1346–1348 (.

* cited by examiner

*Primary Examiner*—Elizabeth Kemmerer
*Assistant Examiner*—Eileen B. O'Hara
(74) *Attorney, Agent, or Firm*—Human Genome Sciences, Inc.

(57) ABSTRACT

The present invention relates to a novel member of the tumor necrosis factor family of receptors. In particular, isolated nucleic acid molecules are provided encoding the human TR9 receptor. TR9 polypeptides are also provided as are vectors, host cells and recombinant methods for producing the same. The invention further relates to screening methods for identifying agonists and antagonists of TR9 receptor activity.

88 Claims, 9 Drawing Sheets

Figure 1A

```
            10                  30                  50
GCGGGCTGCAGTCGCGGCGGCTTCTCCCCGCCTGGGCGGCCGCGCCGCTGGGCAGGTGCT
            70                  90                  110
GAGCGCCCCTAGAGCCTCCCTTGCCGCCTCCCTCCTCTGCCCGGCCGCAGCAGTGCACAT
            130                 150                 170
GGGGTGTTGGAGGTAGATGGGCTCCCGGCCCGGGAGGCGGCGGTGGATGCGGCGCTGGGC
            190                 210                 230
AGAAGCAGCCGCCGATTCCAGCTGCCCCGCGCGCCCCGGGCGCCCCTGCGAGTCCCCGGT
            250                 270                 290
TCAGCCATGGGGACCTCTCCGAGCAGCAGCACCGCCCTCGCCTCCTGCAGCCGCATCGCC
             M  G  T  S  P  S  S  S  T  A  L  A  S  C  S  R  I  A
            310                 330                 350
CGCCGAGCCACAGCCACGATGATCGCGGGCTCCCTTCTCCTGCTTGGATTCCTTAGCACC
 R  R  A  T  A  T  M  I  A  G  S  L  L  L  L  G  F  L  S  T
            370                 390                 410
ACCACAGCTCAGCCAGAACAGAAGGCCTCGAATCTCATTGGCACATACCGCCATGTTGAC
 T  T  A  Q  P  E  Q  K  A  S  N  L  I  G  T  Y  R  H  V  D
            430                 450                 470
CGTGCCACCGGCCAGGTGCTAACCTGTGACAAGTGTCCAGCAGGAACCTATGTCTCTGAG
 R  A  T  G  Q  V  L  T  C  D  K  C  P  A  G  T  Y  V  S  E
            490                 510                 530
CATTGTACCAACACAAGCCTGCGCGTCTGCAGCAGTTGCCCTGTGGGGACCTTTACCAGG
 H  C  T  N  T  S  L  R  V  C  S  S  C  P  V  G  T  F  T  R
            550                 570                 590
CATGAGAATGGCATAGAGAAATGCCATGACTGTAGTCAGCCATGCCCATGGCCAATGATT
 H  E  N  G  I  E  K  C  H  D  C  S  Q  P  C  P  W  P  M  I
            610                 630                 650
GAGAAATTACCTTGTGCTGCCTTGACTGACCGAGAATGCACTTGCCCACCTGGCATGTTC
 E  K  L  P  C  A  A  L  T  D  R  E  C  T  C  P  P  G  M  F
            670                 690                 710
CAGTCTAACGCTACCTGTGCCCCCCATACGGTGTGTCCTGTGGGTTGGGGTGTGCGGAAG
 Q  S  N  A  T  C  A  P  H  T  V  C  P  V  G  W  G  V  R  K
            730                 750                 770
AAAGGGACAGAGACTGAGGATGTGCGGTGTAAGCAGTGTGCTCGGGGTACCTTCTCAGAT
 K  G  T  E  T  E  D  V  R  C  K  Q  C  A  R  G  T  F  S  D
            790                 810                 830
GTGCCTTCTAGTGTGATGAAATGCAAAGCATACACAGACTGTCTGAGTCAGAACCTGGTG
 V  P  S  S  V  M  K  C  K  A  Y  T  D  C  L  S  Q  N  L  V
            850                 870                 890
GTGATCAAGCCGGGGACCAAGGAGACAGACAACGTCTGTGGCACACTCCCGTCCTTCTCC
 V  I  K  P  G  T  K  E  T  D  N  V  C  G  T  L  P  S  F  S
            910                 930                 950
AGCTCCACCTCACCTTCCCCTGGCACAGCCATCTTTCCACGCCCTGAGCACATGGAAACC
 S  S  T  S  P  S  P  G  T  A  I  F  P  R  P  E  H  M  E  T
            970                 990                 1010
CATGAAGTCCCTTCCTCCACTTATGTTCCCAAAGGCATGAACTCAACAGAATCCAACTCT
 H  E  V  P  S  S  T  Y  V  P  K  G  M  N  S  T  E  S  N  S
```

Figure 1B

```
           1030                1050                1070
TCTGCCTCTGTTAGACCAAAGGTACTGAGTAGCATCCAGGAAGGGACAGTCCCTGACAAC
 S  A  S  V  R  P  K  V  L  S  S  I  Q  E  G  T  V  P  D  N
           1090                1110                1130
ACAAGCTCAGCAAGGGGGAAGGAAGACGTGAACAAGACCCTCCCAAACCTTCAGGTAGTC
 T  S  S  A  R  G  K  E  D  V  N  K  T  P  N  L  Q  V  V
           1150                1170                1190
AACCACCAGCAAGGCCCCCACCACAGACACATCCTGAAGCTGCTGCCGTCCATGGAGGCC
 N  H  Q  Q  G  P  H  H  R  H  I  L  K  L  L  P  S  M  E  A
           1210                1230                1250
ACTGGGGGCGAGAAGTCCAGCACGCCCATCAAGGGCCCCAAGAGGGGACATCCTAGACAG
 T  G  G  E  K  S  S  T  P  I  K  G  P  K  R  G  H  P  R  Q
           1270                1290                1310
AACCTACACAAGCATTTTGACATCAATGAGCATTTGCCCTGGATGATTGTGCTTTTCCTG
 N  L  H  K  H  F  D  I  N  E  H  L  P  W  M  I  V  L  F  L
           1330                1350                1370
CTGCTGGTGCTTGTGGTGATTGTGGTGTGCAGTATCCGGAAAAGCTCGAGGACTCTGAAA
 L  L  V  L  V  V  I  V  V  C  S  I  R  K  S  S  R  T  L  K
           1390                1410                1430
AAGGGGCCCCGGCAGGATCCCAGTGCCATTGTGGAAAAGGCAGGGCTGAAGAAATCCATG
 K  G  P  R  Q  D  P  S  A  I  V  E  K  A  G  L  K  K  S  M
           1450                1470                1490
ACTCCAACCCAGAACCGGGAGAAATGGATCTACTACTGCAATGGCCATGGTATCGATATC
 T  P  T  Q  N  R  E  K  W  I  Y  Y  C  N  G  H  G  I  D  I
           1510                1530                1550
CTGAAGCTTGTAGCAGCCCAAGTGGGAAGCCAGTGGAAAGATATCTATCAGTTTCTTTGC
 L  K  L  V  A  A  Q  V  G  S  Q  W  K  D  I  Y  Q  F  L  C
           1570                1590                1610
AATGCCAGTGAGAGGGAGGTTGCTGCTTTCTCCAATGGGTACACAGCCGACCACGAGCGG
 N  A  S  E  R  E  V  A  A  F  S  N  G  Y  T  A  D  H  E  R
           1630                1650                1670
GCCTACGCAGCTCTGCAGCACTGGACCATCCGGGGCCCCGAGGCCAGCCTCGCCCAGCTA
 A  Y  A  A  L  Q  H  W  T  I  R  G  P  E  A  S  L  A  Q  L
           1690                1710                1730
ATTAGCGCCCTGCGCCAGCACCGGAGAAACGATGTTGTGGAGAAGATTCGTGGGCTGATG
 I  S  A  L  R  Q  H  R  R  N  D  V  V  E  K  I  R  G  L  M
           1750                1770                1790
GAAGACACCACCCAGCTGGAAACTGACAAACTAGCTCTCCCGATGAGCCCCAGCCCGCTT
 E  D  T  T  Q  L  E  T  D  K  L  A  L  P  M  S  P  S  P  L
           1810                1830                1850
AGCCCGAGCCCCATCCCCAGCCCCAACGCGAAACTTGAGAATTCCGCTCTCCTGACGGTG
 S  P  S  P  I  P  S  P  N  A  K  L  E  N  S  A  L  L  T  V
           1870                1890                1910
GAGCCTTCCCCACAGGACAAGAACAAGGGCTTCTTCGTGGATGAGTCGGAGCCCTTCTC
 E  P  S  P  Q  D  K  N  K  G  F  F  V  D  E  S  E  P  L  L
           1930                1950                1970
CGCTGTGACTCTACATCCAGCGGCTCCTCCGCGCTGAGCAGGAACGGTTCCTTTATTACC
 R  C  D  S  T  S  S  G  S  S  A  L  S  R  N  G  S  F  I  T
```

Figure 1c

```
              1990                  2010                  2030
AAAGAAAAGAAGGACACAGTGTTGCGGCAGGTACGCCTGGACCCCTGTGACTTGCAGCCT
 K  E  K  K  D  T  V  L  R  Q  V  R  L  D  P  C  D  L  Q  P
              2050                  2070                  2090
ATCTTTGATGACATGCTCCACTTTCTAAATCCTGAGGAGCTGCGGGTGATTGAAGAGATT
 I  F  D  D  M  L  H  F  L  N  P  E  E  L  R  V  I  E  E  I
              2110                  2130                  2150
CCCCAGGCTGAGGACAAACTAGACCGGCTATTCGAAATTATTGGAGTCAAGAGCCAGGAA
 P  Q  A  E  D  K  L  D  R  L  F  E  I  I  G  V  K  S  Q  E
              2170                  2190                  2210
GCCAGCCAGACCCTCCTGGACTCTGTTTATAGCCATCTTCCTGACCTGCTGTAGAACATA
 A  S  Q  T  L  L  D  S  V  Y  S  H  L  P  D  L  L  *
              2230                  2250                  2270
GGGATACTGCATTCTGGAAATTACTCAATTTAGTGGCAGGGTGGTTTTTTAATTTTCTTC
              2290                  2310                  2330
TGTTTCTGATTTTTGTTGTTTGGGTGTGTGTGTGTGTTTGTGTGTGTGTGTGTGTGTGT
              2350                  2370                  2390
GTGTGTGTGTGTGTGTGTGTTTAACAGAGAATATGGCCAGTGCTTGAGTTCTTTCTCC
              2410                  2430                  2450
TTCTCTCTCTCTTTTTTTTTAAATAACTCTTCTGGGAAGTTGGTTTATAAGCCTTTGCC
              2470                  2490                  2510
AGGTGTAACTGTTGTGAAATACCCACCACTAAAGTTTTTTAAGTTCCATATTTCTCCAT
              2530                  2550                  2570
TTTGCCTTCTTATGTATTTTCGAGATTATTCTGTGCACTTTAAATTTACTTAACTTACCA
              2590                  2610                  2630
TAAATGCAGTGTGACTTTTCCCACACACTGGATTGTGAGGCTCTTAACTTCTTAAAAGTA
              2650                  2670                  2690
TAATGGCATCTTGTGAATCCTATAAGCAGTCTTTATGTCTCTTAACATTCACACCTACTT
              2710                  2730                  2750
TTTAAAAACAAATATTATTACTATTTTTATTATTGTTTGTCCTTTATAAATTTTCTTAAA
              2770                  2790                  2810
GATTAAGAAAATTTAAGACCCCATTGAGTTACTGTAATGCAATTCAACTTTGAGTTATCT
              2830                  2850                  2870
TTTAAATATGTCTTGTATAGTTCATATTCATGGCTGAAACTTGACCACACTATTGCTGAT
              2890                  2910                  2930
TGTATGGTTTTCACCTGGACACCGTGTAGAATGCTTGATTACTTGTACTCTTCTTATGCT
              2950                  2970                  2990
AATATGCTCTGGGCTGGAGAAATGAAATCCTCAAGCCATCAGGATTTGCTATTTAAGTGG
              3010                  3030                  3050
CTTGACAACTGGGCCACCAAAGAACTTGAACTTCACCTTTTAGGATTTGAGCTGTTCTGG
              3070                  3090                  3110
AACACATTGCTGCACTTTGGAAAGTCAAAATCAAGTGCCAGTGGCGCCCTTTCCATAGAG
              3130                  3150                  3170
AATTTGCCCAGCTTTGCTTTAAAAGATGTCTTGTTTTTTATATACACATAATCAATAGGT
              3190                  3210                  3230
CCAATCTGCTCTCAAGGCCTTGGTCCTGGTGGGATTCCTTCACCAATTACTTTAATTAAA
              3250                  3270                  3290
AATGGCTGCAACTGTAAGAACCCTTGTCTGATATATTTGCAACTATGCTCCCATTTACAA
```

Figure 1D

```
       3310                  3330                  3350
ATGTACCTTCTAATGCTCAGTTGCCAGGTTCCAATGCAAAGGTGGCGTGGACTCCCTTTG
       3370                  3390                  3410
TGTGGGTGGGGTTTGTGGGTAGTGGTGAAGGACCGATATCAGAAAAATGCCTTCAAGTGT
       3430                  3450                  3470
ACTAATTTATTAATAAACATTAGGTGTTTGTTAAAAAAAAAAAAAAAAAAAAAAA
```

1 MGTSPSSSTALASCSRIARRATATMIAGSLLLLGFLSTTTAQPEQKASNLIGTYRHVDRATGQVLTCDKC 70
PAGTYVSEHCTNTSLRVCSSCPVGTFTRHENGIEKCHDCSQPCPWPMIEKLPCAALFDRECTCPPGMFQS 140
NATCAPHTVCPVGWGVRKKGTETEDVRCKQCARGTFSDVPSSVMKCKAYTDCLSQNLVVIKPGTKETDNV 210
CGTLPSFSSSTSPSPGTAIFPRPEHMETHEVPSSTYVPKGMNSTESNSSASVRPKVLSSIQEGTVPDNTS 280
SARGKEDVNKTLPNLQVVNHQQGPHHRHILKLLPSMEATGGEKSSTPIKGPKRGHPRQNLIIKHFDINEHIL 350
PWMIVLFLLLVLVLVVCSIRKSSRTLKKGPRQDPSAIVEKAGLKKSMTPTQNREKWIYYCNGHGIDLLK 420
LVAAQVGSQWKDIYQFLCNASEREVAAFSNGYTADHERAYAALQHWTIRGPEASLAQLISALRQHRRNDV 490
VEKIRGLMEDTTQLETDKLALPMSPSPLSPSPIPSPNAKLENSALLTVEPSPQDKNKGFFVDESEPLLRC 560
DSTSSGSSALSRNGSFITKEKKDTVLRQVRLDPCDLQPIFDDMLHFLNPEELRVIEEIPQAEDKLDILFE 630
IIGVKSQEASQTLLDSVYSHLPDLL 655

Figure 4B

```
T C D K C P A G T Y V S E H C T N T S L R V C S S C P V G T F T R H E N G I E K     TR9(65-105)
L C D K C A P G T Y L K Q H C T A K W K L P C A A L P D H Y Y T D S W I T S D E E    OPG(40-80)

C H D C S Q P C P W P M I E K L P C A A L D R E C T C P P G M F Q N A T C A          TR9(106-145)
Q L C T L P W V C K E H H Q I Y V K Q E C N R T H N R V C E C K E G R Y L E F E C L   OPG(81-120)

P H T V C P V G W G V R K K G T E T E D V R C K Q C A R G T F S D V P S S V M K      TR9(148-185)
K H R S C P P G Q G V V Q A G T P E R N T V G F R C R Q P D G F R R N E T G B K A P  OPG(121-160)

C K A Y T D C L S Q N L V V I K P G T K E T D N V                                    TR9(186-212)
C R K H T N C S V F G L L L T Q K G N A T H D N I C S                                OPG(161-186)
```

HUMAN TUMOR NECROSIS FACTOR RECEPTOR TR9

This application claims the benefit of the filing date of Provisional Application No. 60/052,991, filed Jun. 11, 1997, which is herein incorporated by reference in its entirety.

FIELD OF THE INVENTION

The present invention relates to a novel member of the tumor necrosis factor family of receptors. More specifically, isolated nucleic acid molecules are provided encoding a novel human tumor necrosis factor receptor, TR9 (also known as Death Domain Containing Receptor 6, or simply DR6). TR9 polypeptides are also provided, as are vectors, host cells and recombinant methods for producing the same. The invention further relates to screening methods for identifying agonists and antagonists of TR9 activity.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-1BBLL; OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga. et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen et al., Science 259:990 (1993)). Targeted mutations of the low affinity nerve growth factor receptor cause a disorder characterized by faulty sensory innovation of peripheral structures (Lee et al., Cell 69:737 (1992)).

TNF and LT-α are capable of binding to two TNF receptors (the 55- and 75-kd TNF receptors). A large number of biological effects elicited by TNF and LT-∝, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler et al., Science 264:667–668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)).

Apoptosis, or programmed cell death, is a physiologic process essential to the normal development and homeostasis of multicellular organisms (Steller, Science 267:1445–1449 (1995)). Derangements of apoptosis contribute to the pathogenesis of several human diseases including cancer, neurodegenerative disorders, and acquired immune deficiency syndrome (Thompson C. B., Science 267:1456–1462 (1995)). Recently, much attention has focused on the signal transduction and biological function of two cell surface death receptors, Fas/APO-1 and TNFR-1 (Cleveland et al., Cell 81:479–482 (1995); Fraser et al., Cell 85:781–784 (1996); S. Nagata et al., Science 267:1449–56 (1995)). Both are members of the TNF receptor family, which also include TNFR-2, low affinity NGFR, CD40, and CD30, among others (Smith et al., Science 248:1019–23 (1990); Tewari et al., in Modular Texts in Molecular and Cell Biology; M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the Drosophila suicide gene, reaper (Golstein et al., Cell 81:185–6 (1995); White et al., Science 264:677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (Chinnaiyan et al., Cell 81:505–512 (1995); Boldin et al., J. Biol. Chem. 270:7795–8 (1995); Kischkel et al., EMBO 14:5579–5588 (1995)), which in turn binds and presumably activates FLICE/MACH1, a member of the ICE/CED-3 family of pro-apoptotic proteases (Muzio et al., Cell 85:817–827 (1996); Boldin et al., Cell 85:803–815 (1.996)). While the central role of Fas/APO-1 is to trigger cell death, TNFR-1 can signal an array of diverse biological activities-many of which stem from its ability to activate NF-kB (Tartaglia et al., Immunol Today 13:151–153 (1992)). Accordingly, TNFR-1 recruits the multivalent adapter molecule TRADD, which like FADD, also contains a death domain (Hsu et al., Cell 81:495–504 (1995); Hsu et al., Cell 84:299–308 (1996)). Through its associations with a number of signaling molecules including FADD, TRAF2, and RIP, TRADD can signal both apoptosis and NF-kB activation (Hsu et al., Cell 84:299–308 (1996); Hsu et al., Immunity 4:387–396 (1996)).

The effects of TNF family ligands and receptors are varied and influence numerous functions, both normal and abnormal, in the biological processes of the mammalian system. There is a clear need, therefore, for identification and characterization of additional novel TNF receptors and ligands that influence biological activity, both normally and in disease states.

SUMMARY OF THE INVENTION

The present invention provides isolated nucleic acid molecules comprising a polynucleotide encoding the TR9 receptor having the amino acid sequence shown in FIGS. 1A–D (SEQ ID NO:2) or the amino acid sequence encoded by the cDNA clone deposited as ATCC Deposit Number 209037 on May 15, 1997.

The present invention also relates to recombinant vectors, which include the isolated nucleic acid molecules of the present invention, and to host cells containing the recombinant vectors, as well as to methods of making such vectors and host cells and for using them for production of TR9 receptor polypeptides or peptides by recombinant techniques.

The invention further provides an isolated TR9 polypeptide having an amino acid sequence encoded by a polynucleotide described herein.

The present invention also provides a screening method for identifying compounds capable of enhancing or inhibiting a cellular response induced by the TR9 receptor. The method involves contacting cells which express the TR9 receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

The invention further provides diagnostic assays such as quantitative and diagnostic assays for detecting levels of TR9 receptor protein. Thus, for instance, a diagnostic assay in accordance with the invention for detecting overexpression of TR9, or soluble form thereof, compared to normal control tissue samples, may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

Thus, the invention further provides a method for enhancing apoptosis induced by a TNF-family ligand, which involves administering to a cell which expresses the TR9 polypeptide an effective amount of an agonist capable of increasing TR9 mediated signaling. Preferably, TR9 mediated signaling is increased to treat a disease wherein decreased apoptosis is exhibited.

In a further aspect, the present invention is directed to a method for inhibiting apoptosis induced by a TNF-family ligand, which involves administering to a cell which expresses the TR9 polypeptide an effective amount of an antagonist capable of decreasing TR9 mediated signaling. Preferably, TR9 mediated signaling is decreased to treat a disease wherein increased apoptosis is exhibited.

BRIEF DESCRIPTION OF THE FIGURES

FIGS. 1A–D shows the nucleotide sequence (SEQ ID NO:1) and deduced amino acid sequence (SEQ ID NO:2) of the TR9 receptor. Analysis using the computer program PSORT reveals that the protein has a predicted leader sequence of about 40 amino acid residues (underlined) and a deduced molecular weight of about 72 kDa. It is further predicted that amino acid residues from about 41 to about 350 constitute the extracellular domain (amino acid residues from about 1 to about 310 in SEQ ID NO:2); from about 351 to about 367 the transmembrane domain (amino acid residues from about 311 to about 327 in SEQ ID NO:2); from about 368 to about 655 the intracellular domain (amino acid residues from about 328 to about 615 in SEQ ID NO:2); and from about 429 to about 495 the death domain (amino acid residues from about 389 to about 455 in SEQ ID NO:2).

FIG. 2 shows the regions of similarity between the amino acid sequences of the TR9 receptor protein and Fas (SEQ ID NO:3), NGFR p75 (SEQ ID NO:4), and TNFR 1 (SEQ ID NO:5).

FIGS. 4A–C. Highlights of the predicted amino acid sequence of TR9.

FIG. 4A: The open reading frame for TR9 defines a type I transmembrane protein of 655 amino acids (SEQ ID NO:2). Application of a computer program other than PSORT has predicted the mature protein to start at amino acid 42 (Gln, indicated by a black triangle). The putative signal peptide and transmembrane domain are single and double underlined, respectively. Six potential N-glycosylation sites are indicated by black dots. The cytoplasmic death domain is boxed. An intracellular region containing a potential leucine-zipper motif overlapping with a proline rich sequence is underlined with a thick line. FIG. 4B: Sequence alignment of extracellular cysteine-rich domains of TR9 (SEQ ID NO:19) and osteoprotegrin (SEQ ID NO:20). Alignment was done with Megalign (DNASTAR) software. Shading represents identical residues. FIG. 4C: Sequence comparison of death domains of TR9 (SEQ ID NO:21), CD95 (SEQ ID NO:22), TNFR1 (SEQ ID NO:23), DR3 (SEQ ID NO:24), DR4 (SEQ ID NO:25), and DR5 (SEQ ID NO:26). Alignment was performed and represented in the same way as in FIG. 4B. OPG; osteoprotegerin.

DETAILED DESCRIPTION OF THE PREFERRED EMBODIMENTS

Figure 2:
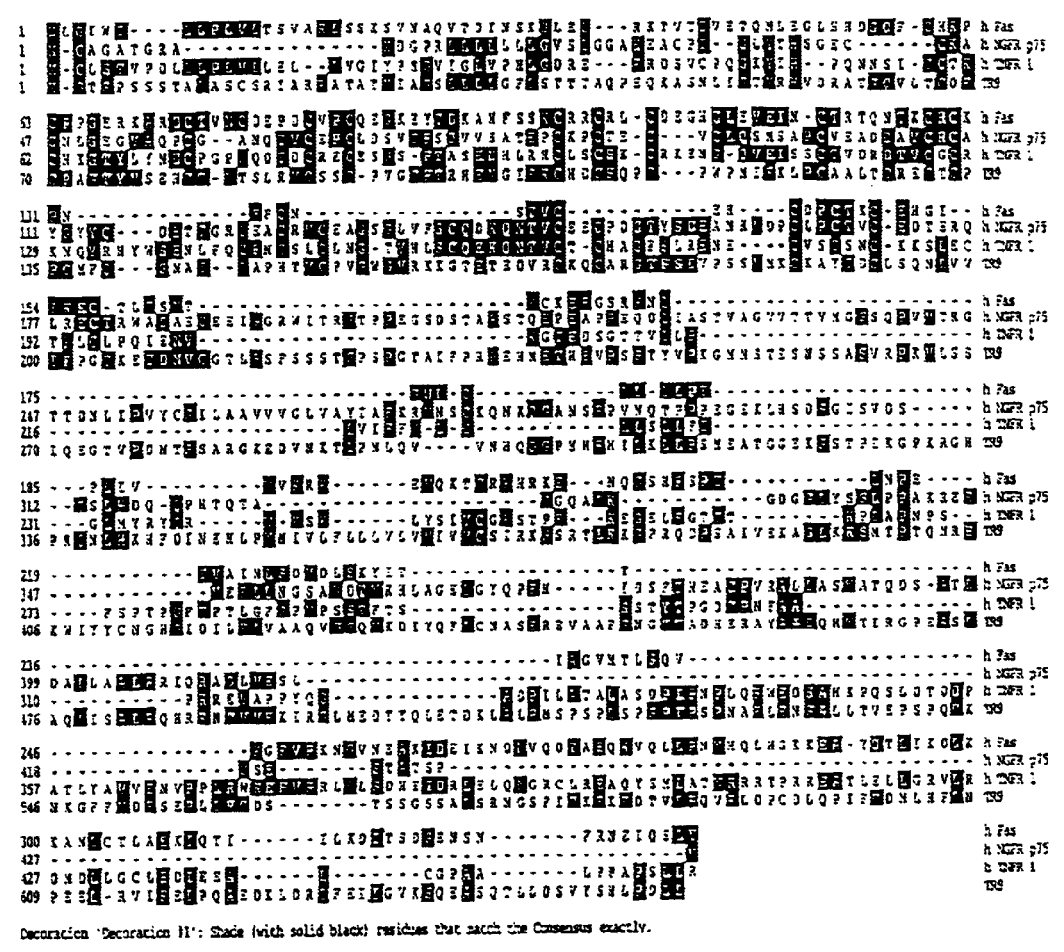
Figure 3:
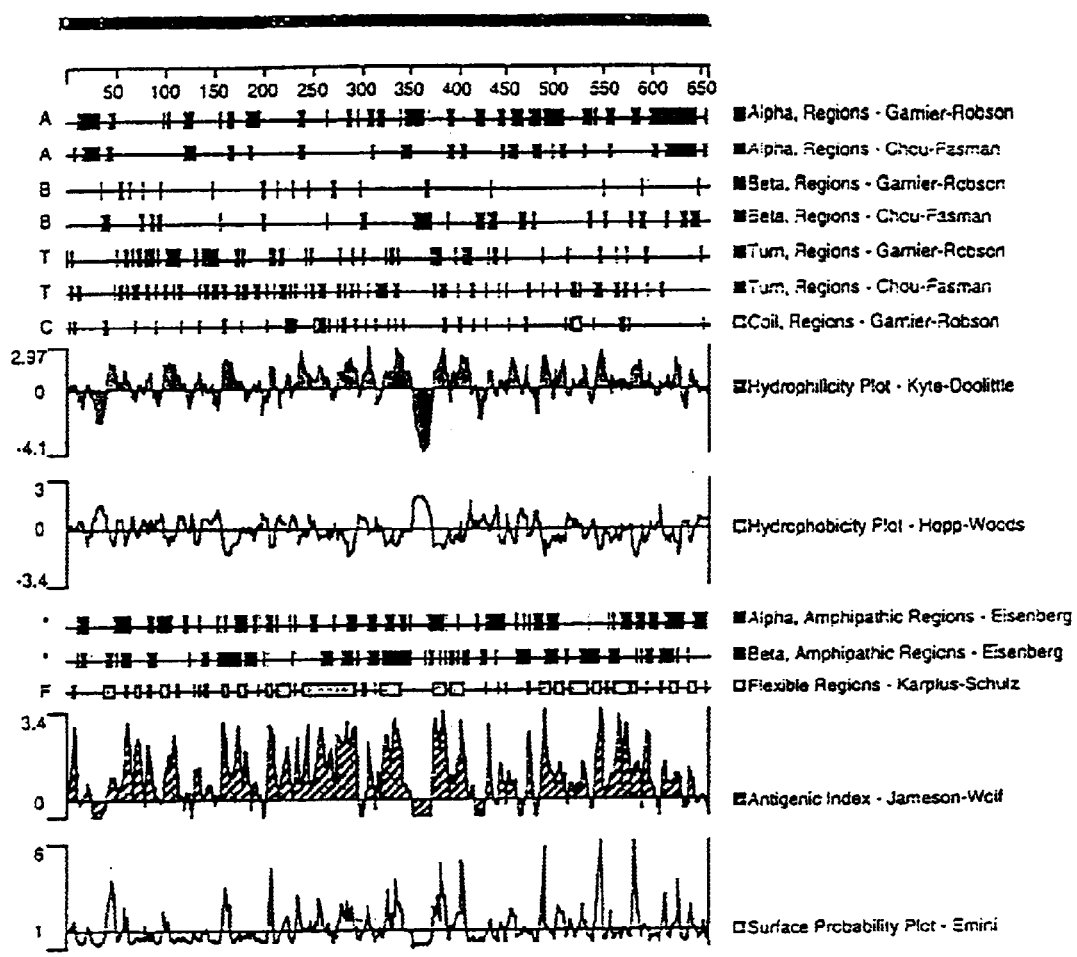
FIG. 3 shows an analysis of the TR9 amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues about 44 to about 121, about 156 to about 311, about 323 to about 348, about 376 to about 412, about 433 to about 474, about 485 to about 599, and about 611 to about 628 in FIGS. 1A–D correspond to the shown highly antigenic regions of the TR9 protein. These highly antigenic fragments in FIGS. 1A–D correspond to the following fragments, respectively, in SEQ ID NO:2: amino acid residues about 4 to about 81, about 116 to about 271, about 283 to about 308, about 336 to about 372, about 393 to about 434, about 445 to about 559, and about 571 to about 588.

The present invention provides isolated nucleic acid molecules comprising a polynucleotide encoding a TR9 receptor polypeptide having the amino acid sequence shown in FIGS. 1A–C (SEQ ID NO:2), which was determined by sequencing a cloned cDNA. As shown in FIG. 2, the TR9 receptor protein of the present invention shares sequence homology with Fas (SEQ ID NO:3), NGFR p75 (SEQ ID NO:4), and TNFR 1(SEQ ID NO:5). The nucleotide sequence shown in SEQ ID NO:1 was obtained by sequencing a cDNA clone, which was deposited on May 15, 1997 at the American Type Culture Collection, 10801 University Boulevard Manassas Va. 20110-2209 and given accession number 209037. The deposited clone is inserted in the pBluescript SK(–) plasmid (Stratagene, La Jolla, Calif.) using the EcoRI and XhoI restriction endonuclease cleavage sites.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–D (SEQ ID NO:1), a nucleic acid molecule of the present invention encoding a TR9 polypeptide may be obtained using standard cloning and screening procedures, such as those for cloning cDNAs using mRNA as starting material. Illustrative of the invention, the nucleic acid molecule described in FIGS. 1A–D (SEQ ID NO:1) was discovered in a cDNA library derived from human microvascular endothelial cells. The gene was also identified in cDNA libraries from the following tissues: human placenta, stromal cells, human amygdala, human umbilical vein endothelial cells, kidney cancer, human gall bladder, soares adult brain, normal human liver hepatocellular tumor, keratinocytes, bone marrow, macrophage, human synovial sarcoma, human hippocampus, and human tonsils.

The determined nucleotide sequence of the TR9 cDNA of FIGS. 1A–D (SEQ ID NO:1) contains an open reading frame encoding a protein of about 615 amino acid residues, with a predicted leader sequence of about 40 amino acid residues, and a deduced molecular weight of about 72 kDa. The amino acid sequence of the predicted mature TR9 receptor is shown in FIGS. 1A–D (SEQ ID NO:2) from amino acid residue about 1 to residue about 615. The TR9 protein shown in FIGS. 1A–D (SEQ ID NO:2) is about 24% identical and about 43% similar to NGFR (FIG. 2).

Figure 6:
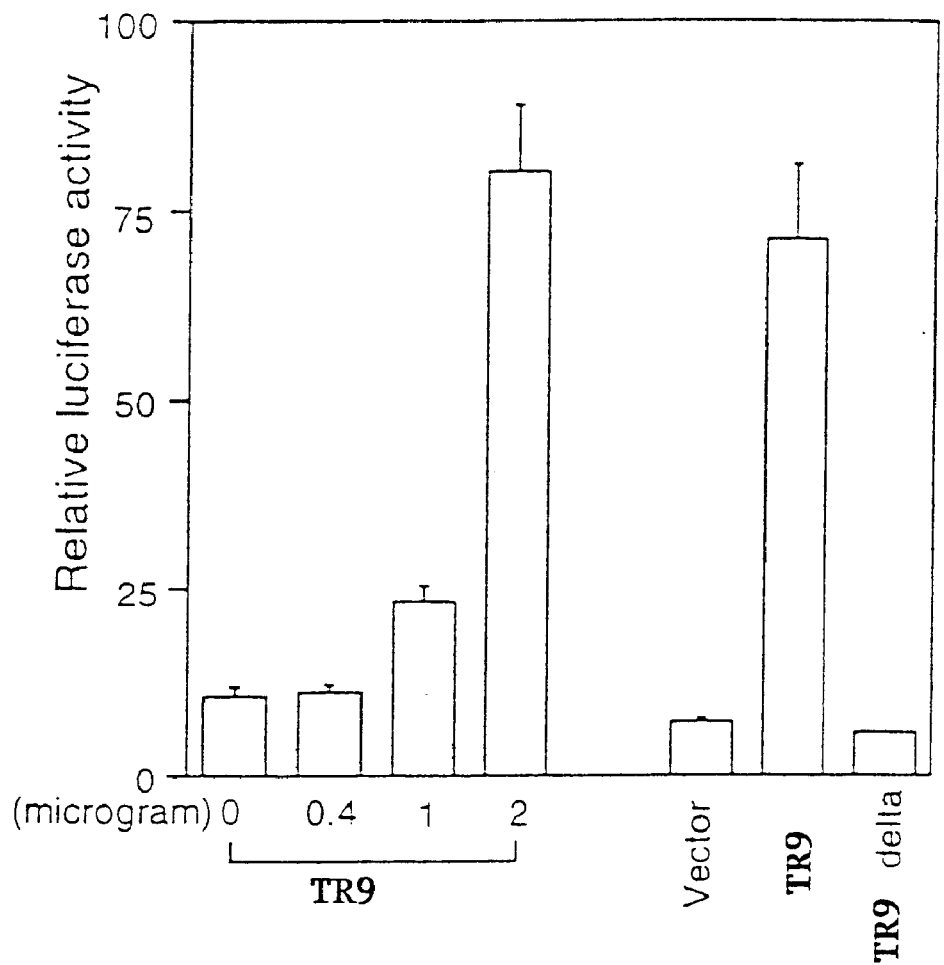
FIG. 6. TR9 mediates nuclear factor kB activation. Cotransfection of 293 cells was performed with the indicated expression constructs and a NF-kB luciferase reporter construct. After transfection (at 36 hours), cell extracts were prepared and luciferase activities determined as previously described (Chinnaiyan et al., Science 274:990–992 (1996); and Pan et al., Science 276:111–113 (1997)). Transfection efficiency was monitored by β-galactosidase activity. A portion of the transfected cells was used to monitor expression of TR9 or TR9 delta. Cell lysates were prepared and immunoprecipitated with FLAG M2 affinity gel and the presence of TR9 or TR9 delta detected by blotting with anti-FLAG.

As predicted by the sequence homology exhibited between TR9 and other death domain containing receptors (see FIG. 4C), TR9 induces of mammalian cells apoptosis (see FIG. 6). It is expected that TR9-induced apoptosis will be efficiently blocked by inhibitors of death proteases including z-VAD-fmk, an irreversible broad spectrum caspase inhibitor and CrmA, a cowpox virus encoded serpin that preferentially inhibits apical caspases such as FLICE/MACH-1 (caspase-8).

As indicated, the present invention also provides the mature form(s) of the TR9 receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TR9 receptor polypeptides having the amino acid sequence encoded by the cDNA clone contained in the host identified as ATCC Deposit No. 209037 and as shown in FIGS. 1A–D (SEQ ID NO:2). By the mature TR9 protein having the amino acid sequence encoded by the cDNA clone contained in the host identified as ATCC Deposit 209037 is meant the mature form(s) of the TR9 receptor produced by expression in a mammalian cell (e.g., COS cells, as described below) of the complete open reading frame encoded by the human DNA sequence of the clone contained in the vector in the deposited host. As indicated below, the mature TR9 receptor having the amino acid sequence encoded by the cDNA clone contained in ATCC Deposit No. 209037 may or may not differ from the predicted "mature" TR9 receptor protein shown in SEQ ID NO:2 (amino acids from about 1 to about 615) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete TR9 polypeptides of the present invention were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acid residues 40 and 41 in FIGS. 1A–D (amino acid residues −1 and 1 in SEQ ID NO:2). Thereafter, the complete amino acid sequences were further analyzed by visual inspection, applying a simple form of the (−1,−3) rule of von Heinje. von Heinje, supra. Thus, the leader sequence for the TR9 receptor protein is predicted to consist of amino acid residues from about 1 to 40 in FIGS. 1A–D (amino acid residues −40 to about −1 in SEQ ID NO:2), while the mature TR9 protein is predicted to consist of residues from about 41 to 655 in FIGS. 1A–D (about 1 to about 615 of SEQ ID NO:2). Analysis using a different computer program predicts that the mature protein of TR9 starts at amino acid 42 (Gln) as depicted in FIGS. 1A–D and 4A. The results of this analysis are presented in FIG. 4A and described in Example 6.

As one of ordinary skill would appreciate, due to the possibility of sequencing errors, as well as the variability of cleavage sites for leaders in different known proteins, the predicted TR9 receptor polypeptide encoded by the deposited cDNA comprises about 655 amino acids, but may be anywhere in the range of 645–665 amino acids; and the predicted leader sequence of this protein is about 40 amino acids, but may be anywhere in the range of about 30 to about 50 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A–D (SEQ ID NO:1); DNA molecules comprising the coding sequence for the mature TR9 protein; and DNA molecules which comprise a sequence substantially different from those described above but which, due to the degeneracy of the genetic code, still encode the TR9 protein shown in FIGS. 1A–D (SEQ ID NO:2). Of course, the genetic code is well known in the art. Thus, it would be routine for one skilled in the art to generate such degenerate variants.

In addition, the invention provides nucleic acid molecules having nucleotide sequences related to extensive portions of the nucleotide sequence in FIGS. 1A–D of (SEQ ID NO:1), which have been determined from the following related cDNA clones: HIBEJ86R (SEQ ID NO:6), HL1AA79R (SEQ ID NO:7), HHFGD57R (SEQ ID NO:8), HSABG38R (SEQ ID NO:9), and HHPDZ31R (SEQ ID NO:10).

Further, the invention includes a polynucleotide comprising any portion of at least about 30 nucleotides, preferably at least about 50 nucleotides, of the nucleotide sequence disclosed in FIGS. 1A–D from nucleotides 655 to 907 (nucleotides 615 to 867 of SEQ ID NO:1) and/or the nucleotide sequence disclosed in FIGS. 1A–D from nucleotides to 540 to 1020 (nucleotides 500 to 980 as depicted in SEQ ID NO:1).

In another aspect, the invention provides isolated nucleic acid molecules encoding the TR9 receptor polypeptide having an amino acid sequence as encoded by the cDNA clone contained in the plasmid deposited as ATCC Deposit No. 209037 on May 15, 1997. In a further embodiment, nucleic acid molecules are provided encoding the mature TR9 receptor polypeptide or the full-length TR9 receptor polypeptide lacking the N-terminal methionine. The invention also provides an isolated nucleic acid molecule having the nucleotide sequence shown in FIGS. 1A–D (SEQ ID NO:1) or the nucleotide sequence of the TR9 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the TR9 receptor gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA, or the nucleotide sequence shown in FIGS. 1A–D (SEQ ID NO:1), or the complementary strand thereto, is intended fragments at least about 15 nt, and more preferably at least about 20 nt, still more preferably at least about 30 nt, and even more preferably, at least about 40, 50, 100, 150, 200, 250, 300, 400, or 500 nt in length. These fragments have numerous uses which include, but are not limited to, diagnostic probes and primers as discussed herein. Of course, larger fragments 50–1500 nt in length are also useful according to the present invention as are fragments corresponding to most, if not all, of the nucleotide sequence of the deposited cDNA or as shown in FIGS. 1A–D (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A–D (SEQ ID NO:1).

Representative examples of TR9 polynucleotide fragments of the invention include, for example, fragments that comprise, or alternatively, consist of, a sequence from about nucleotide 1–50, 51–100, 101–150, 151–200, 201–250, 251–300, 301–350, 351–400, 401–450, 445–879, 451–500, 501–550, 551–600, 615–651, 651–700, 701–750, 751–800, 800–850, 850–867, 851–900, 901–950, 951–1000, 1001–1050, 1051–1100, 1101–1150, 1151–1200, 1201–1250 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, 2001–2050, 2051–3000, or 3001 to the end of SEQ ID NO:1, or the complementary DNA strand thereto, or the cDNA contained in the deposited clone. In this context "about" includes the particularly recited ranges, larger or smaller by several (5, 4, 3, 2, or 1) nucleotides, at either terminus or at both termini. In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete or mature TR9 polypeptide. Such functional activities include, but are not limited to, biological activity, antigenicity [ability to bind (or compete with a TR9 polypeptide for binding) to an anti-TR9 antibody], immunogenicity (ability to generate antibody which binds to a TR9 polypeptide), and ability to bind to a receptor or ligand for a TR9 polypeptide.

Preferred nucleic acid fragments of the present invention include nucleic acid molecules encoding: a polypeptide comprising the TR9 receptor extracellular domain (predicted to constitute amino acid residues from about 1 to about 310 in SEQ ID NO:2); a polypeptide comprising the four TNFR-like cysteine rich motifs of TR9 (amino acid residues 67 to 211 in FIGS. 1A–D; amino acid residues 27 to 171 in SEQ ID NO:2), a polypeptide comprising the TR9 receptor transmembrane domain (predicted to constitute amino acid residues from about 311 to about 327 in SEQ ID NO:2); a polypeptide comprising the TR9 receptor intracellular domain (predicted to constitute amino acid residues from about 328 to about 615 in SEQ ID NO:2); a polypeptide comprising the TR9 receptor extracellular and intracellular domains with all or part of the transmembrane domain deleted; a polypeptide comprising the TR9 receptor death domain (predicted to constitute amino acid residues from about 389 to about 455 in SEQ ID NO:2); and nucleic acid molecules encoding epitope bearing portions of the TR9 receptor protein. As above, with the leader sequence, the amino acid residues constituting the TR9 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding one or more epitope-bearing portions of the TR9 receptor protein. In particular, such nucleic acid fragments of the present invention include nucleic acid molecules encoding: a polypeptide comprising amino acid residues from about 4 to about 81 in SEQ ID NO:2; a polypeptide comprising amino acid residues from about 116 to about 271 in SEQ ID NO:2; a polypeptide comprising amino acid residues from about 283 to about 308 in SEQ ID NO:2; a polypeptide comprising amino acid residues from about 336 to about 372 in SEQ ID NO:2; a polypeptide comprising amino acid residues from about 393 to about 434 in SEQ ID NO:2; a polypeptide comprising amino acid residues from about 445 to about 559 in SEQ ID NO:2; and a polypeptide comprising amino acid residues from about 571 to about 588 in SEQ ID NO:2. The inventors have determined that the above polypeptide fragments are antigenic regions of the TR9 receptor. Methods for determining other such epitope-bearing portions of the TR9 protein are described in detail below.

In another aspect, the invention provides an isolated nucleic acid molecule comprising a polynucleotide which hybridizes, preferably under stringent hybridization conditions, to a portion of the polynucleotide sequence of a polynucleotide of the invention such as, for instance, the cDNA clone contained in ATCC Deposit 209037. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70, or 80–150 nt, or the entire length of the reference polynucleotide. These are useful as diagnostic probes and primers as discussed above and in more detail below.

In specific embodiments, polynucleotides of the invention hybridize to a complementary strand of a polynucleotide encoding amino acid residues 40–152, 40–48, 40–51, 51–66, 66–73, 73–83, 83–104, 104–110, 110–128, 128–146, and/or 146–152 as depicted in SEQ ID NO:2.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–D (SEQ ID NO:1).

Of course, a polynucleotide which hybridizes only to a poly A sequence (such as the 3' terminal poly tract of the TR9 receptor cDNA shown in SEQ ID NO:1), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

As indicated, nucleic acid molecules of the present invention which encode a TR9 receptor polypeptide may include, but are not limited to, those encoding the amino acid sequence of the mature polypeptide, by itself; the coding sequence for the mature polypeptide and additional sequences, such as those encoding the about amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the TR9 receptor fused to Fc at the N- or C-terminus.

The present invention further relates to variants of the nucleic acid molecules of the present invention, which encode portions, analogs or derivatives of the TR9 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR9 receptor or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the polypeptide having the amino acid sequence shown in FIGS. 1A–D (SEQ ID NO:2); (b) a nucleotide sequence encoding the polypeptide having the amino acid sequence shown in FIGS. 1A–D (SEQ ID NO:2), but lacking the N-terminal methionine; (c) a nucleotide sequence encoding the predicted mature TR9 polypeptide (full-length polypeptide with any attending leader sequence removed) comprising the amino acid sequence at positions from about 1 to about 615 in SEQ ID NO:2; (d) a nucleotide sequence encoding the TR9 polypeptide having the amino acid sequence encoded by the cDNA clone contained in ATCC Deposit No. 209037; (e) a nucleotide sequence encoding the mature TR9 polypeptide having the amino acid sequence encoded by the cDNA clone contained in ATCC Deposit No. 209037; (f) a nucleotide sequence encoding the TR9 receptor extracellular domain; (g) a nucleotide sequence encoding the four TNFR-like cysteine rich motifs of TR9 (amino acid residues 67 to 211 in FIGS. 1A–D; amino acid residues 27 to 171 in SEQ ID NO:2); (h) a nucleotide sequence encoding the TR9 receptor transmembrane domain; (i) a nucleotide sequence encoding the TR9 receptor intracellular domain; (j) a nucleotide sequence encoding the TR9 receptor extracellular and intracellular domains with all or part of the transmembrane domain deleted; (k) a nucleotide sequence encoding the TR9 receptor death domain; (l) a nucleotide sequence encoding the TR9 leucine zipper; and (m) a nucleotide sequence complementary to any of the nucleotide sequences in (a), (b), (c), (d), (e), (f), (g), (h), (i), (j), (k), or (l).

By a polynucleotide having a nucleotide sequence at least, for example, 95% "identical" to a reference nucleotide sequence encoding a TR9 receptor polypeptide is intended that the nucleotide sequence of the polynucleotide is identical to the reference sequence except that the polynucleotide sequence may include up to five point mutations per each 100 nucleotides of the reference nucleotide sequence encoding the TR9 receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR9 nucleotide sequence shown in FIGS. 1A–D (SEQ ID NO:1) or any fragment as described herein.

As a practical matter, whether any particular nucleic acid molecule is at least 90%, 95%, 96%, 97%, 98% or 99% identical to, for instance, the nucleotide sequence shown in FIGS. 1A–D (SEQ ID NO:1) or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequence shown in FIGS. 1A–D (SEQ ID NO:1) or to the nucleic acid sequence of the deposited cDNA, irrespective of whether they encode a polypeptide having TR9 receptor activity. This is because even where a particular nucleic acid molecule does not encode a polypeptide having TR9 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR9 receptor activity include, inter alia, (1) isolating the TR9 receptor gene or allelic variants thereof in a cDNA library; (2) in situ hybridization (e.g., "FISH") to metaphase chromosomal spreads to provide precise chromosomal location of the TR9 receptor gene, as described in Verma et al., *Human Chromosomes: A Manual of Basic Techniques*, Pergamon Press, N.Y. (1988); and (3) Northern Blot analysis for detecting TR9 receptor mRNA expression in specific tissues.

Preferred, however, are nucleic acid molecules having sequences at least 90%, 95%, 96%, 97%, 98% or 99% identical to the nucleic acid sequence shown in FIGS. 1A–D (SEQ ID NO:1), the nucleic acid sequence of the deposited cDNA, or fragments thereof, which do, in fact, encode a polypeptide having TR9 receptor activity. By "a polypeptide having TR9 receptor activity" is intended polypeptides exhibiting activity similar, but not necessarily identical, to an activity of the TR9 receptor of the invention (either the full-length protein or, preferably, the mature protein), as measured in a particular immunoassay and/or biological assay. For example, TR9 receptor activity can be measured using the cell death assays performed essentially as previously described (Chinnaiyan et al., Cell 81:505–512 (1995); Boldin et al., *J. Biol. Chem.* 270:7795–8(1995); Kischkel et al., *EMBO* 14:5579–5588 (1995); Chinnaiyan et al., *J. Biol Chem.* 271:4961–4965 (1996)) and as set forth in Example 5 below. In MCF7 cells, plasmids encoding full-length TR9 or a candidate death domain containing receptor are co-transfected with the pLantern reporter construct encoding green fluorescent protein. Nuclei of cells transfected with TR9 will exhibit apoptotic morphology as assessed by DAPI staining. It is expected that like TNFR-1 and Fas/APO-1 (Muzio et al., Cell 85:817–827 (1996); Boldin et al., Cell 85:803–815 (1996); Tewari et al., *J. Biol. Chem.* 270:3255–60 (1995)), TR9-induced apoptosis will be blocked by the inhibitors of ICE-like proteases, CrmA and z-VAD-fmk. In addition, it is expected that apoptosis induced by TR9 will be blocked by dominant negative versions of FADD (FADD-DN) or FLICE (FLICE-DN/MACHa1C360S).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A–D (SEQ ID NO:1), or fragments thereof, will encode a polypeptide "having TR9 receptor activity." In fact, since degenerate variants of these nucleotide sequences all encode the same polypeptide, in many instances, this will be clear to the skilled artisan even without performing the above described assay. It will be further recognized in the art that, for such nucleic acid molecules that are not degenerate variants, a reasonable number will also encode a polypeptide having TR9 receptor activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Polynucleotide Assays

This invention is also related to the use of TR9 polynucleotides to detect complementary polynucleotides such as, for example, as a diagnostic reagent. Detection of a mutated form of TR9 associated with a dysfunction will provide a diagnostic tool that can add or define a diagnosis of a disease or susceptibility to a disease which results from under-expression over-expression or altered expression of TR9 or a soluble form thereof, such as, for example, tumors or autoimmune disease.

Individuals carrying mutations in the TR9 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding TR9 can be used to identify and analyze TR9 expression and mutations. For example, deletions and insertions can be detected by a change in size of the amplified product in comparison to the normal genotype. Point mutations can be identified by hybridizing amplified DNA to radiolabeled TR9. RNA or alternatively, radiolabeled TR9 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and Sl protection or the chemical cleavage method (e.g., Cotton et al., *Proc. Natl. Acad Sci. USA* 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include the isolated DNA molecules of the present invention, host cells which are genetically engineered with the recombinant vectors, or which are otherwise engineered to produce the polypeptides of the invention, and the production of TR9 receptor polypeptides, or fragments thereof, by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the DNA of the invention is operatively associated with an appropriate heterologous regulatory element (e.g., promoter or enhancer), such as, the phage lambda PL promoter, the *E. coli* lac, trp, and tac promoters, the SV40 early and late promoters and promoters of retroviral LTRs, to name a few. Other suitable promoters will be known to the skilled artisan.

In embodiments in which vectors contain expression constructs, these constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

The present invention also relates to host cells containing the vector constructs discussed herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EPA 0 232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, Bennett et al., *J. of Molec. Recognition* 8:52–58 (1995) and Johanson et al., *J. Biol. Chem.* 270:9459–9471 (1995).

The TR9 receptor can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue or alternatively, may be missing the N-terminal methionine, in some cases as a result of host-mediated processes.

TR9 receptor polynucleotides and polypeptides may be used in accordance with the present invention for a variety of applications, particularly those that make use of the chemical and biological properties of TR9. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of TR9 by an agonist. Additional applications relate to diagnosis and to treatment of disorders of cells, tissues and organisms. These aspects of the invention are discussed further below.

TR9 Receptor Polypeptides and Fragments

The invention further provides an isolated TR9 receptor polypeptide having the amino acid sequence encoded by the deposited cDNA, or the amino acid sequence in FIGS. 1A–D (SEQ ID NO:2), or a peptide or polypeptide comprising a portion of the above polypeptides.

The polypeptides of this invention may be membrane bound or may be in a soluble circulating form. Soluble peptides are defined by amino acid sequence wherein the sequence comprises the polypeptide sequence lacking the transmembrane domain.

The polypeptides of the present invention may exist as a membrane bound receptor having a transmembrane region and an intra- and extracellular region or they may exist in soluble form wherein the transmembrane domain is lacking. One example of such a form of the TR9 receptor is the TR9 receptor shown in FIGS. 1A–D (SEQ ID NO:2) which contains, in addition to a leader sequence, transmembrane, intracellular and extracellular domains. Thus, this form of the TR9 receptor appears to be localized in the cytoplasmic membrane of cells which express this protein.

It will be recognized in the art that some amino acid sequences of the TR9 receptor can be varied without significant effect on the structure or function of the protein. If such differences in sequence are contemplated, it should be remembered that there will be critical areas on the protein which determine activity. Thus, the invention further includes variations of the TR9 receptor which show substantial TR9 receptor activity or which include regions of TR9 receptor protein such as the protein portions discussed below. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," *Science* 247:1306–1310 (1990).

Thus, the fragment, derivative or analog of the polypeptide of FIGS. 1A–D (SEQ ID NO:2), or that encoded by the deposited cDNA, may be: (i) one in which one or more of the amino acid residues are substituted with a conserved or non-conserved amino acid residue (preferably a conserved amino acid residue(s), and more preferably at least one but less than ten conserved amino acid residues), and such substituted amino acid residue(s) may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR9 receptor. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993), describes certain mutations resulting in selective binding of TNF-α to only one of the two known types of TNF receptors. Thus, the TR9 receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–D and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

Amino acids in the TR9 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR9 receptor can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids about −40 to about 615 in SEQ ID NO:2; a polypeptide comprising amino acids about −39 to about 615 in SEQ ID NO:2; a polypeptide comprising amino acids about 1 to about 615 in SEQ ID NO:2; a polypeptide comprising the extracellular domain; a polypeptide comprising the four TNFR-like cysteine rich motifs of TR9 (amino acid residues 67 to 211 in FIGS. 1A–D; amino acid residues 27–171 in SEQ ID NO:2); a polypeptide comprising the transmembrane domain; a polypeptide comprising the intracellular domain; a polypeptide comprising the extracellular and intracellular domains with all or part of the transmembrane domain deleted; a polypeptide comprising the death domain (amino acid residues 429–495 as depicted in FIGS. 1A–D; amino acid residues 389–455 in SEQ ID NO:2); and/or a polypeptide comprising the TR9 leucine zipper (amino acid residues 497–518 of FIGS. 1A–D; amino acid residues 457–478 of SEQ ID NO:2); as well as polypeptides which are at least 80% identical, more preferably at least 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a TR9 receptor polypeptide is intended that the amino acid sequence of the polypeptide is identical to the reference sequence except that the polypeptide sequence may include up to five amino acid alterations per each 100 amino acids of the reference amino acid of the TR9 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–D (SEQ ID NO: 2), the amino acid sequence encoded by deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses which include, but are not limited to, molecular weight marker on SDS-PAGE gels or on molecular sieve gel filtration columns using methods well known to those of skill in the art.

For many proteins, including the extracellular domain of a membrane associated protein or the mature form(s) of a secreted protein, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other TR9 functional activities may still be retained. For example, in many instances, the ability of the shortened protein to induce and/or bind to antibodies which recognize TR9 (preferably antibodies that bind specifically to TR9) will retained irrespective of the size or location of the deletion. Whether a particular polypeptide lacking N-terminal and/or C-terminal residues of a complete protein retains such immunologic activities can readily be determined by routine methods described herein and otherwise known in the art.

In one embodiment, the present invention further provides polypeptides having one or more residues deleted from the amino terminus of the amino acid sequence of the TR9 polypeptide depicted in FIGS. 1A–D (SEQ ID NO:2) or encoded by the cDNA of the deposited clone. Particularly, in one embodiment, N-terminal deletions of the TR9 polypeptide can be described by the general formula m to 615, where m is a number from −39 to 614 corresponding to the position of amino acid identified in SEQ ID NO:2 and preferably, corresponds to one of the N-terminal amino acid residues identified in the N-terminal deletions specified herein. In specific embodiments, N-terminal deletions of the TR9 polypeptide of the invention comprise, or alternatively consist of, amino acid residues: Q-2 to L-615; P-3 to L-615; E-4 to L-615; Q-5 to L-615; K-6 to L-615; A-7 to L-615; S-8 to L-615; N-9 to L-615; L-10 to L-615; I-11 to L-615; G-12 to L-615; T-13 to L-615; Y-14 to L-615; R-15 to L-615; H-16 to L-615; V-17 to L-615; D-18 to L-615; R-19 to L-615; A-20 to L-615; T-21 to L-615; G-22 to L-615; Q-23 to L-615; V-24 to L-615; L-25 to L-615; T-26 to L-615; C-27 to L-615; D-28 to L-615; K-29 to L-615; C-30 to L-615; P-31 to L-615; A-32 to L-615; G-33 to L-615; T-34 to L-615; Y-35 to L-615; V-36 to L-615; S-37; to L-615; E-38 to L-615; H-39 to L-615; C-40 to L-615; T-41 to L-615; N-42 to L-615; T-43 to L-615; S-44 to L-615; L-45 to L-615; R-46 to L-615; V-47 to L-615; C-48; to L-615; S-49 to L-615; S-50 to L-615; C-51 to L-615; P-52 to L-615; V-53 to L-615; G-54 to L-615; T-55 to L-615; F-56 to L-615; T-57 to L-615; R-58 to L-615; H-59; to L-615; E-60 to L-615; N-61 to L-615; G-62 to L-615; I-63 to L-615; E-64 to L-615; K-65 to L-615; C-66 to L-615; H-67 to L-615; D-68 to L-615; C-69 to L-615; S-70 to L-615; Q-71 to L-615; P-72 to L-615; C-73 to L-615; P-74 to L-615; W-75 to L-615; P-76 to L-615; M-77 to L-615; I-78 to L-615; E-79 to L-615; K-80 to L-615; L-81 to L-615; P-82 to L-615; C-83 to L-615; A-84 to L-615; A-85 to L-615; L-86 to L-615; T-87 to L-615; D-88 to L-615; R-89 to L-615; E-90 to L-615; C-91 to L-615; T-92 to L-615; C-93 to L-615; P-94 to L-615; P-95 to L-615; G-96 to L-615; M-97 to L-615; F-98 to L-615; Q-99 to L-615; S-100 to L-615; N-101 to L-615; A-102 to L-615; T-103 to L-615; C-104 to L-615; A-105 to L-615; P-106 to L-615; H-107 to L-615; T-108 to L-615; V-109 to L-615; C-110 to L-615; P-111 to L-615; V-112 to L-615; G-113 to L-615; W-114 to L-615; G-115 to L-615; V-116 to L-615; R-117 to L-615; K-118 to L-615; K-119 to L-615; G-120 to L-615; T-121 to L-615; E-122 to L-615; T-123 to L-615; E-124 to L-615; D-125 to L-615; V-126 to L-615; R-127 to L-615; C-128 to L-615; K-129 to L-615; Q-130 to L-615; C-131 to L-615; A-132 to L-615; R-133 to L-615; G-134 to L-615; T-135 to L-615; F-136 to L-615; S-137 to L-615; D-138 to L-615; V-139 to L-615; P-140 to L-615; S-141 to L-615; S-142 to L-615; V-143 to L-615; M-144 to L-615; K-145 to L-615; C-146 to L-615; K-147 to L-615; A-148 to L-615; Y-149 to L-615; T-150 to L-615; D-151 to L-615; C-152 to L-615; L-153 to L-615; S-154 to L-615; Q-155 to L-615; N-156 to L-615; L-157 to L-615; V-158 to L-615; V-159 to L-615; I-160 to L-615; K-161 to L-615; P-162 to L-615; G-163 to L-615; T-164 to L-615; K-165 to L-615; E-166 to L-615; T-167 to L-615; D-168 to L-615; N-169 to L-615; V-170 to L-615; C-171 to L-615; G-172 to L-615; T-173 to L-615; L-174 to L-615; P-175 to L-615; S-176 to L-615; F-177 to L-615; S-178 to L-615; S-179 to L-615; S-180 to L-615; T-181 to L-615; S-182 to L-615; P-183 to L-615; S-184 to L-615; P-185 to L-615;

G-186 to L-615; T-187 to L-615; A-188 to L-615; I-189 to L-615; F-190 to L-615; P-191 to L-615; R-192 to L-615; P-193 to L-615; E-194 to L-615; H-195 to L-615; M-196 to L-615; E-197 to L-615; T-198 to L-615; H-199 to L-615; E-200 to L-615; V-201 to L-615; P-202 to L-615; S-203 to L-615; S-204 to L-615; T-205 to L-615; Y-206 to L-615; V-207 to L-615; P-208 to L-615; K-209 to L-615; G-210 to L-615; M-211 to L-615; N-212 to L-615; S-213 to L-615; T-214 to L-615; E-215 to L-615; S-216 to L-615; N-217 to L-615; S-218 to L-615; S-219 to L-615; A-220 to L-615; S-221 to L-615; V-222 to L-615; R-223 to L-615; P-224 to L-615; K-225 to L-615; V-226 to L-615; L-227 to L-615; S-228 to L-615; S-229 to L-615; I-230 to L-615; Q-231 to L-615; E-232 to L-615; G-233 to L-615; T-234 to L-615; V-235 to L-615; P-236 to L-615; D-237 to L-615; N-238 to L-615; T-239 to L-615; S-240 to L-615; S-241 to L-615; A-242 to L-615; R-243 to L-615; G-244 to L-615; K-245 to L-615; E-246 to L-615; D-247 to L-615; V-248 to L-615; N-249 to L-615; K-250 to L-615; T-251 to L-615; L-252 to L-615; P-253 to L-615; N-254 to L-615; L-255 to L-615; Q-256 to L-615; V-257 to L-615; V-258 to L-615; N-259 to L-615; H-260 to L-615; Q-261 to L-615; Q-262 to L-615; G-263 to L-615; P-264 to L-615; H-265 to L-615; H-266 to L-615; R-267 to L-615; H-268 to L-615; I-269 to L-615; L-270 to L-615; K-271 to L-615; L-272 to L-615; L-273 to L-615; P-274 to L-615; S-275 to L-615; M-276 to L-615; E-277 to L-615; A-278 to L-615; T-279 to L-615; G-280 to L-615; G-281 to L-615; E-282 to L-615; K-283 to L-615; S-284 to L-615; S-285 to L-615; T-286 to L-615; P-287 to L-615; I-288 to L-615; K-289 to L-615; G-290 to L-615; P-291 to L-615; K-292 to L-615; R-293 to L-615; G-294 to L-615; H-295 to L-615; P-296 to L-615; R-297 to L-615; Q-298 to L-615; N-299 to L-615; L-300 to L-615; H-301 to L-615; K-302 to L-615; H-303 to L-615; F-304 to L-615; D-305 to L-615; I-306 to L-615; N-307 to L-615; E-308 to L-615; H-309 to L-615; L-310 to L-615; P-311 to L-615; W-312 to L-615; M-313 to L-615; I-314 to L-615; V-315 to L-615; L-316 to L-615; F-317 to L-615; L-318 to L-615; L-319 to L-615; L-320 to L-615; V-321 to L-615; L-322 to L-615; V-323 to L-615; V-324 to L-615; I-325 to L-615; V-326 to L-615; V-327 to L-615; C-328 to L-615; S-329 to L-615; I-330 to L-615; R-331 to L-615; K-332 to L-615; S-333 to L-615; S-334 to L-615; R-335 to L-615; T-336 to L-615; L-337 to L-615; K-338 to L-615; K-339 to L-615; G-340 to L-615; P-341 to L-615; R-342 to L-615; Q-343 to L-615; D-344 to L-615; P-345 to L-615; S-346 to L-615; A-347 to L-615; I-348 to L-615; V-349 to L-615; E-350 to L-615; K-351 to L-615; A-352 to L-615; G-353 to L-615; L-354 to L-615; K-355 to L-615; K-356 to L-615; S-357 to L-615; M-358 to L-615; T-359 to L-615; P-360 to L-615; T-361 to L-615; Q-362 to L-615; N-363 to L-615; R-364 to L-615; E-365 to L-615; K-366 to L-615; W-367 to L-615; I-368 to L-615; Y-369 to L-615; Y-370 to L-615; C-371 to L-615; N-372 to L-615; G-373 to L-615; H-374 to L-615; G-375 to L-615; I-376 to L-615; D-377 to L-615; I-378 to L-615; L-379 to L-615; K-380 to L-615; L-381 to L-615; V-382 to L-615; A-383 to L-615; A-384 to L-615; Q-385 to L-615; V-386 to L-615; G-387 to L-615; S-388 to L-615; Q-389 to L-615; W-390 to L-615; K-391 to L-615; D-392 to L-615; I-393 to L-615; Y-394 to L-615; Q-395 to L-615; F-396 to L-615; L-397 to L-615; C-398 to L-615; N-399 to L-615; A-400 to L-615; S-401 to L-615; E-402 to L-615; R-403 to L-615; E-404 to L-615; V-405 to L-615; A-406 to L-615; A-407 to L-615; F-408 to L-615; S-409 to L-615; N-410 to L-615; G-411 to L-615; Y-412 to L-615; T-413 to L-615; A-414 to L-615; D-415 to L-615; H-416 to L-615; E-417 to L-615; R-418 to L-615; A-419 to L-615; Y-420 to L-615; A-421 to L-615; A-422 to L-615; L-423 to L-615; Q-424 to L-615; H-425 to L-615; W-426 to L-615; T-427 to L-615; I-428 to L-615; R-429 to L-615; G-430 to L-615; P-431 to L-615; E-432 to L-615; A-433 to L-615; S-434 to L-615; L-435 to L-615; A-436 to L-615; Q-437 to L-615; L-438 to L-615; I-439 to L-615; S-440 to L-615; A-441 to L-615; L-442 to L-615; R-443 to L-615; Q-444 to L-615; H-445 to L-615; R-446 to L-615; R-447 to L-615; N-448 to L-615; D-449 to L-615; V-450 to L-615; V-451 to L-615; E-452 to L-615; K-453 to L-615; I-454 to L-615; R-455 to L-615; G-456 to L-615; L-457 to L-615; M-458 to L-615; E-459 to L-651; D-460 to L-615; T-461 to L-615; T-462 to L-615; Q-463 to L-615; L-464 to L-615; E-465 to L-615; T-466 to L-615; D-467 to L-615; K-468 to L-615; L-469 to L-615; A-470 to L-615; L-471 to L-615; P-472 to L-615; M-473 to L-615; S-474 to L-615; P-475 to L-615; S-476 to L-615; P-477 to L-615; L-478 to L-615; S-479 to L-615; P-480 to L-615; S-481 to L-615; P-482 to L-615; I-483 to L-615; P-484 to L-615; S-485 to L-615; P-486 to L-615; N-487 to L-615; A-488 to L-615; K-489 to L-615; L-490 to L-615; E-491 to L-615; N-492 to L-615; S-493 to L-615; A-494 to L-615; L-495 to L-615; L-496 to L-615; T-497 to L-615; V-498 to L-615; E-499 to L-615; P-500 to L-615; S-501 to L-615; P-502 to L-615; Q-503 to L-615; D-504 to L-615; K-505 to L-615; N-506 to L-615; K-507 to L-615; G-508 to L-615; F-509 to L-615; F-510 to L-615; V-511 to L-615; D-512 to L-615; E-513 to L-615; S-514 to L-615; E-515 to L-615; P-516 to L-615; L-517 to L-615; L-518 to L-615; R-519 to L-615; C-520 to L-615; D-521 to L-615; S-522 to L-615; T-523 to L-615; S-524 to L-615; S-525 to L-615; G-526 to L-615; S-527 to L-615; S-528 to L-615; A-529 to L-615; L-530 to L-615; S-531 to L-615; R-532 to L-615; N-533 to L-615; G-534 to L-615; S-535 to L-615; F-536 to L-615; I-537 to L-615; T-538 to L-615; K-539 to L-615; E-540 to L-615; K-541 to L-615; K-542 to L-615; D-543 to L-615; T-544 to L-615; V-545 to L-615; L-546 to L-615; R-547 to L-615; Q-548 to L-615; V-549 to L-615; R-550 to L-615; L-551 to L-615; D-552 to L-615; P-553 to L-615; C-554 to L-615; D-555 to L-615; L-556 to L-615; Q-557 to L-615; P-558 to L-615; I-559 to L-615; F-560 to L-615; D-561 to L-615; D-562 to L-615; M-563 to L-615; L-564 to L-615; H-565 to L-615; F-566 to L-615; L-567 to L-615; N-568 to these polypeptides are also encompassed by the invention.

In another embodiment, N-terminal deletions of the TR9 polypeptide can be described by the general formula m to 310 where m is a number from −40 to 309 corresponding to the amino acid sequence identified in SEQ ID NO:2. In specific embodiments, N terminal deletions of the TR9 of the invention comprise, or alternatively, consist of, amino acid residues: Q-2 to L-310; P-3 to L-310; E-4 to L-310: Q-5 to L-310; K-6 to L-310; A-7 to L-310; S-8 to L-310; N-9 to L-310; L-10 to L-310; I-11 to L-310; G-12 to L-310; T-13 to L-310; Y-14 to L-310; R-15 to L-310; H-16 to L-310; V-17 to L-310; D-18 to L-310; R-19 to L-310; A-20 to L-310; T-21 to L-310; G-22 to L-310; Q-23 to L-310; V-24 to L-310; L-25 to L-310; T-26 to L-310; C-27 to L-310; D-28 to L-310; K-29 to L-310; C-30 to L-310; P-31 to L-310; A-32 to L-310; G-33 to L-310; T-34 to L-310; Y-35 to L-310; V-36 to L-310; S-37 to L-310; E-38 to L-310; H-39 to L-310; C-40 to L-310; T-41 to L-310; N-42 to L-310; T-43 to L-310; S-44 to L-310; L-45 to L-310; R-46 to L-310; V-47 to L-310; C-48 to L-310; S-49 to L-310; S-50 to L-310; C-51 to L-310; P-52 to L-310; V-53 to L-310; G-54 to L-310; T-55 to L-310; F-56 to L-310; T-57 to L-310; R-58 to L-310; H-59 to L-310; E-60 to L-310; N-61 to L-310; G-62 to L-310; I-63 to L-310; E-64 to L-310; K-65 to L-310; C-66 to L-310; H-67 to L-310; D-68 to L-310; C-69 to L-310; S-70 to L-310; Q-71 to L-310; P-72 to L-310; C-73 to L-310; P-74 to L-310; W-75 to L-310; P-76 to L-310; M-77 to L-310; I-78 to L-310; E-79 to L-310; K-80 to L-310; L-81 to L-310; P-82 to L-310; C-83 to L-310; A-84 to L-310; A-85 to L-310; L-86 to L-310; T-87 to L-310; D-88 to L-310; R-89 to L-310; E-90 to L-310; C-91 to L-310; T-92 to L-310; C-93 to L-310; P-94 to L-310; P-95 to L-310; G-96 to L-310; M-97 to L-310; F-98 to L-310; Q-99 to L-310; S-100 to L-310; N-101 to L-310; A-102 to L-310; T-103 to L-310; C-104 to L-310; A-105 to L-310; P-106 to L-310; H-107 to L-310; T-108 to L-310; V-109 to L-310; C-110 to L-310; P-111 to L-310; V-112 to L-310; G-113 to L-310; W-114 to L-310; G-115 to L-310; V-116 to L-310; R-117 to L-310; K-118 to L-310; K-119 to L-310; G-120 to L-310; T-121 to L-310; E-122 to L-310; T-123 to L-310; E-124 to L-310; D-125 to L-310; V-126 to L-310; R-127 to L-310; C-128 to L-310; K-129 to L-310; Q-130 to L-310; C-131 to L-310; A-132 to L-310; R-133 to L-310; G-134 to L-310; T-135 to L-310; F-136 to L-310; S-137 to L-310; D-138 to L-310; V-139 to L-310; P-140 to L-310; S-141 to L-310; S-142 to L-310; V-143 to L-310; M-144 to L-310; K-145 to L-310; C-146 to L-310; K-147 to L-310; A-148 to L-310; Y-149 to L-310; T-150 to L-310; D-151 to L-310; C-152 to L-310; L-153 to L-310; S-154 to L-310; Q-155 to L-310; N-156 to L-310; L-157 to L-310; V-158 to L-310; V-159 to L-310; I-160 to L-310; K-161 to L-310; P-162 to L-310; G-163 to L-310; T-164 to L-310; K-165 to L-310; E-166 to L-310; T-167 to L-310; D-168 to L-310; N-169 to L-310; V-170 to L-310; C-171 to L-310; G-172 to L-310; T-173 to L-310; L-174 to L-310; P-175 to L-310; S-176 to L-310; F-177 to L-310; S-178 to L-310; S-179 to L-310; S-180 to L-310; T-181 to L-310; S-182 to L-310; P-183 to L-310; S-184 to L-310; P-185 to L-310; G-186 to L-310; T-187 to L-310; A-188 to L-310; I-189 to L-310; F-190 to L-310; P-191 to L-310; R-192 to L-310; P-193 to L-310; E-194 to L-310; H-195 to L-310; M-196 to L-310; E-197 to L-310; T-198 to L-310; H-199 to L-310; E-200 to L-310; V-201 to L-310; P-202 to L-310; S-203 to L-310; S-204 to L-310; T-205 to L-310; Y-206 to L-310; V-207 to L-310; P-208 to L-310; K-209 to L-310; G-210 to L-310; M-211 to L-310; N-212 to L-310; S-213 to L-310; T-214 to L-310; E-215 to L-310; S-216 to L-310; N-217 to L-310; S-218 to L-310; S-219 to L-310; A-220 to L-310; S-221 to L-310; V-222 to L-310; R-223 to L-310; P-224 to L-310; K-225 to L-310; V-226 to L-310; L-227 to L-310; S-228 to L-310; S-229 to L-310; I-230 to L-310; Q-231 to L-310; E-232 to L-310; G-233 to L-310; T-234 to L-310; V-235 to L-310; P-236 to L-310; D-237 to L-310; N-238 to L-310; T-239 to L-310; S-240 to L-310; S-241 to L-310; A-242 to L-310; R-243 to L-310; G-244 to L-310; K-245 to L-310; E-246 to L-310; D-247 to L-310; V-248 to L-310; N-249 to L-310; K-250 to L-310; T-251 to L-310; L-252 to L-310; P-253 to L-310; N-254 to L-310; L-255 to L-310; Q-256 to L-310; V-257 to L-310; V-258 to L-310; N-259 to L-310; H-260 to L-310; Q-261 to L-310; Q-262 to L-310; G-263 to L-310; P-264 to L-310; H-265 to L-310; H-266 to L-310; R-267 to L-310; H-268 to L-310; I-269 to L-310; L-270 to L-310; K-271 to L-310; L-272 to L-310; L-273 to L-310; P-274 to L-310; S-275 to L-310; M-276 to L-310; E-277 to L-310; A-278 to L-310; T-279 to L-310; G-280 to L-310; G-281 to L-310; E-282 to L-310; K-283 to L-310; S-284 to L-310; S-285 to L-310; T-286 to L-310; P-287 to L-310; I-288 to L-310; K-289 to L-310; G-290 to L-310; P-291 to L-310; K-292 to L-310; R-293 to L-310; G-294 to L-310; H-295 to L-310; P-296 to L-310; R-297 to L-310; Q-298 to L-310; N-299 to L-310; L-300 to L-310; H-301 to L-310; K-302 to L-310; H-303 to L-310; F-304 to L-310; D-305 to L-310; of SEQ ID NO:2. Polynucleotides encoding these polypeptides are also encompassed by the invention.

Further embodiments of the invention are directed to C-terminal deletions of the TR9 polypeptide described by the general formula 1 to n, where n is a number from 2 to 614 corresponding to the position of amino acid residue identified in SEQ ID NO:2 and preferably, corresponds to one of the C-terminal amino acid residues identified in the C-terminal deletions specified herein. In specific embodiments, C terminal deletions of the TR9 polypeptide of the invention comprise, or alternatively, consist of, amino acid residues: A-1 to L-614; A-1 to D-613; A-1 to P-612; A-1 to L-611; A-1 to H-610; A-1 to S-609; A-1 to Y-608; A-1 to V-607; A-1 to S-606; A-1 to D-605; A-1 to L-604; A-1 to L-603; A-1 to T-602; A-1 to Q-601; A-1 to S-600; A-1 to A-599; A-1 to E-598; A-1 to Q-597; A-1 to S-596; A-1 to K-595; A-1 to V-594; A-1 to G-593; A-1 to I-592; A-1 to I-591; A-1 to E-590; A-1 to F-589; A-1 to L-588; A-1 to R-587; A-1 to D-586; A-1 to L-585; A-1 to K-584; A-1 to D-583; A-1 to E-582; A-1 to A-581; A-1 to Q-580; A-1 to P-579; A-1 to I-578; A-1 to E-577; A-1 to E-576; A-1 to I-575; A-1 to V-574; A-1 to R-573; A-1 to L-572; A-1 to E-571; A-1 to E-570; A-1 to P-569; A-1 to N-568; A-1 to L-567; A-1 to F-566; A-1 to H-565; A-1 to L-564; A-1 to M-563; A-1 to D-562; A-1 to D-561; A-1 to F-560; A-1 to I-559; A-1 to P-558; A-1 to Q-557; A-1 to L-556; A-1 to D-555; A-1 to C-554; A-1 to P-553; A-1 to D-552; A-1 to L-551; A-1 to R-550; A-1 to V-549; A-1 to Q-548; A-1 to R-547; A-1 to L-546; A-1 to V-545; A-1 to T-544; A-1 to D-543; A-1 to K-542; A-1 to K-541; A-1 to E-540; A-1 to K-539; A-1 to T-538; A-1 to I-537; A-1 to F-536; A-1 to S-535; A-1 to G-534; A-1 to N-533; A-1 to R-532; A-1 to S-531; A-1 to L-530; A-1 to A-529; A-1 to S-528; A-1 to S-527; A-1 to G-526; A-1 to S-525, A-1 to S-524; A-1 to T-523; A-1 to S-522; A-1 to D-521; A-1 to C-520; A-1 to R-519; A-1 to L-518; A-1 to L-517; A-1 to P-516; A-1 to E-515; A-1 to S-514; A-1 to E-513; A-1 to D-512; A-1 to V-511; A-1 to F-510; A-1 to F-509; A-1 to G-508; A-1 to K-507; A-1 to N-506; A-1 to K-505; A-1 to D-504; A-1 to Q-503; A-1 to P-502; A-1 to S-501; A-1 to P-500; A-1 to E-499; A-1 to V-498; A-1 to T-497; A-1 to L-496; A-1 to L-495; A-1 to A-494; A-1 to S-493; A-1 to N-492; A-1 to E-491; A-1 to L-490; A-1 to K-489; A-1 to A-488; A-1 to N-487; A-1 to P-486; A-1 to S-485; A-1 to P-484; A-1 to I-483; A-1 to P-482; A-1 to S-481; A-1 to P-480; A-1 to S-479; A-1 to L-478; A-1 to P-477; A-1 to S-476; A-1 to P-475; A-1 to S-474; A-1 to M-473; A-1 to P-472; A-1 to L-471; A-1 to A-470; A-1 to L-469; A-1 to K-468; A-1 to D-467; A-1 to T-466; A-1 to E-465; A-1 to L-464; A-1 to Q-463; A-1 to T-462; A-1 to T-461; A-1 to D-460; A-1 to E-459; A-1 to M-458; A-1 to L-457; A-1 to G-456; A-1 to R-455; A-1 to I-454; A-1 to K-453; A-1 to E-452; A-1 to V-451; A-1 to V-450; A-1 to D-449; A-1 to N-448; A-1 to R-447; A-1 to R-446; A-1 to H-445; A-1 to Q-444; A-1 to R-443; A-1 to L-442; A-1 to A-441; A-1 to S-440; A-1 to I-439; A-1 to L-438; A-1 to Q-437; A-1 to A-436; A-1 to L-435; A-1 to S-434; A-1 to A-433; A-1 to E-432; A-1 to P-431; A-1 to G-430; A-1 to R-429; A-1 to I-428; A-1 to T-427; A-1 to W-426; A-1 to H-425; A-1 to Q-424; A-1 to L-423; A-1 to A-422; A-1 to A-421; A-1 to Y-420; A-1 to A-419; A-1 to R-418; A-1 to E-417; A-1 to H-416; A-1 to D-415; A-1 to A-414; A-1 to T-413; A-1 to Y-412; A-1 to G-411; A-1 to N-410; A-1 to S-409; A-1 to F-408; A-1 to A-407; A-1 to A-406; A-1 to V-405; A-1 to E-404; A-1 to R-403; A-1 to E-402; A-1 to S-401; A-1 to A-400; A-1 to N-399; A-1 to C-398; A-1 to L-397; A-1 to F-396; A-1 to Q-395; A-1 to Y-394; A-1 to I-393; A-1 to D-392; A-1 to K-391; A-1 to W-390; A-1 to Q-389; A-1 to S-388; A-1 to G-387; A-1 to V-386; A-1 to Q-385; A-1 to A-384; A-1 to A-383; A-1 to V-382; A-1 to L-381; A-1 to K-380; A-1 to L-379; A-1 to I-378; A-1 to D-377; A-1 to I-376; A-1 to G-375; A-1 to H-374; A-1 to G-373; A-1 to N-372; A-1 to C-371; A-1 to Y-370; A-1 to Y-369; A-1 to I-368; A-1 to W-367; A-1 to K-366; A-1 to E-365; A-1 to R-364; A-1 to N-363; A-1 to Q-362; A-1 to T-361; A-1 to P-360; A-1 to T-359; A-1 to M-358; A-1 to S-357; A-1 to K-356; A-1 to K-355; A-1 to L-354; A-1 to G-353; A-1 to A-352; A-1 to K-351; A-1 to E-350; A-1 to V-349; A-1 to I-348; A-1 to A-347; A-1 to S-346; A1 to P-345; A-1 to D-344; A-1 to Q-343; A-1 to R-342; A-1 to P-341; A-1 to G-340; A-1 to K-339; A-1 to K-338; A-1 to L-337; A-1 to T-336; A-1 to R-335; A-1 to S-334; A-1 to S-333; A-1 to K-332; A-1 to R-331; A-1 to I-330; A-1 to S-329; A-1 to C-328; A-1 to V-327; A-1 to V-326; A-1 to I-325; A-1 to V-324; A-1 to V-323; A-1 to L-322; A-1 to V-321; A-1 to L-320; A-1 to L-319; A-1 to L-318; A-1 to F-317; A-1 to L-316; A-1 to V-315; A-1 to I-314; A-1 to M-313; A-1 to W-312; A-1 to P-311; A-1 to L-310; A-1 to H-309; A-1 to E-308; A-1 to N-307; A-1 to I-306; A-1 to D-305; A-1 to F-304; A-1 to H-303; A-1 to K-302; A-1 to H-301; A-1 to L-300; A-1 to N-299; A-1 to Q-298; A-1 to R-297; A-1 to P-296; A-1 to H-295; A-1 to G-294; A-1 to R-293; A-1 to K-292; A-1 to P-291; A-1 to G-290; A-1 to K-289; A-1 to I-288; A-1 to P-287; A-1 to T-286; A-1 to S-285; A-1 to S-284; A-1 to K-283; A-1 to E-282; A-1 to G-281; A-1 to G-280; A-1 to T-279; A-1 to A-278; A-1 to E-277; A-1 to M-276; A-1 to S-275; A-1 to P-274; A-1 to L-273; A-1 to L-272; A-1 to K-271; A-1 to L-270; A-1 to I-269; A-1 to H-268; A-1 to R-267; A-1 to H-266; A-1 to H-265; A-1 to P-264; A-1 to G-263; A-1 to Q-262; A-1 to Q-261; A-1 to H-260; A-1 to N-259; A-1 to V-258; A-1 to V-257; A-1 to Q-256; A-1 to L-255; A-1 to N-254; A-1 to P-253; A-1 to L-252; A-1 to T-251; A-1 to K-250; A-1 to N-249; A-1 to V-248; A-1 to D-247; A-1 to E-246; A-1 to K-245; A-1 to G-244; A-1 to R-243; A-1 to A-242; A-1 to S-241; A-1 to S-240; A-1 to T-239; A-1 to N-238; A-1 to D-237; A-1 to P-236; A-1 to V-235; A-1 to T-234; A-1 to G-233; A-1 to E-232; A-1 to Q-231; A-1 to I-230; A-1 to S-229; A-1 to S-228; A-1 to L-227; A-1 to V-226; A-1 to K-225; A-1 to P-224; A-1 to R-223; A-1 to V-222; A-1 to S-221; A-1 to A-220; A-1 to S-219; A-1 to S-218; A-1 to N-217; A-1 to S-216; A-1 to E-215; A-1 to T-214; A-1 to S-213; A-1 to N-212; A-1 to M-211; A-1 to G-210; A-1 to K-209; A-1 to P-208; A-1 to V-207; A-1 to Y-206; A-1 to T-205; A-1 to S-204; A-1 to S-203; A-1 to P-202; A-1 to V-201; A-1 to E-200; A-1 to H-199; A-1 to T-198; A-1 to E-197; A-1 to M-196; A-1 to H-195; A-1 to E-194; A-1 to P-193; A-1 to R-192; A-1 to P-191; A-1 to F-190; A-1 to I-189; A-1 to A -188; A-1 to T-187; A-1 to G-186; A-1 to P-185; A-1 to S-184; A-1 to P-183; A-1 to S-182; A-1 to T-181; A-1 to S-180; A-1 to S-179; A-1 to S-178; A-1 to F-177; A-1 to S-176; A-1 to P-175; A-1 to L-174; A-1 to T-173; A-1 to G-172; A-1 to C-171; A-1 to V-170; A-1 to N-169; A-1 to D-168; A-1 to T-167; A-1 to E-166; A-1 to K-165; A-1 to T-164; A-1 to G-163; A-1 to P-162; A-1 to K-161; A-1 to I-160; A-1 to V-159; A-1 to V-158; A-1 to L-157; A-1 to N-156; A-1 to Q-155; A-1 to S-154; A-1 to L-153; A-1 to C-152; A-1 to D-151; A-1 to T-150; A-1 to Y-149; A-1 to A-148; A-1 to K-147; A-1 to C-146; A-1 to K-145; A-1 to M-144; A-1 to V-143; A-1 to S-142; A-1 to S-141; A-1 to P-140; A-1 to V-139; A-1 to D-138; A-1 to S-137; A-1 to F-136; A-1 to T-135; A-1 to G-134; A-1 to R-133; A-1 to A-132; A-1 to C-131; A-1 to Q-130; A-1 to K-129; A-1 to C-128; A-1 to R-127; A-1 to V-126; A-1 to D-125; A-1 to E-124; A-1 to T-123; A-1 to E-122; A-1 to T-121; A-1 to G-120; A-1 to K-119; A-1 to K-118; A-1 to R-117; A-1 to V-116; A-1 to G-115; A-1 to W-114; A-1 to G-113; A-1 to V-112; A-1 to P-111; A-1 to C-110; A-1 to V-109; A-1 to T-108; A-1 to H-107; A-1 to P-106; A-1 to A-105; A-1 to C-104; A-1 to T-103; A-1 to A-102; A-1 to N-101; A-1 to S-100; A-1 to Q-99; A-1 to F-98; A-1 to M-97; A-1 to G-96; A-1 to P-95; A-1 to P-94; A-1 to C-93; A-1 to T-92; A-1 to C-91; A-1 to -90; A-1 to R-89; A-1 to D-88; A-1 to T-87; A-1 to L-86; A-1 to A-85; A-1 to A-84; A-1 to C-83; A-1 to P-82; A-1 to L-81; A-1 to K-80; A-1 to E-79; A-1 to I-78; A-1 to M-77; A-1 to P-76; A-1 to W-75; A-1 to P-74; A-1 to C-73; A-1 to P-72; A-1 to Q-71; A-1 to S-70; A-1 to C-69; A-1 to D-68; A-1 to H-67; A-1 to C-66; A-1 to K-65; A-1 to E-64; A-1 to I-63; A-1 to G-62; A-1 to N-61; A-1 to E-60; A-1 to H-59; A-1 to R-58; A-1 to T-57; A-1 to F-56; A-1 to T-55; A-1 to G-54; A-1 to V-53; A-1 to P-52; A-1 to C-51; A-1 to S-50; A-1 to S-49; A-1 to C-48; A-1 to V-47; A-1 to R-46; A-1 to L-45; A-1 to S-44; A-1 to T-43; A-1 to N-42, A-1 to T-41; A-1 to C-40; A-1 to H-39; A-1 to E-38; A-1 to S-37; A-1 to V-36; A-1 to Y-35; A-1 to T-34; A-1 to G-33; A-1 to A-32; A-1 to P-31; A-1 to C-30; A-1 to K-29; A-1 to D-28; A-1 to C-27; A-1 to T-26; A-1 to L-25; A-1 to V-24; A-1 to Q-23; A-1 to G-22; A-1 to T-21; A-to A-20; A-1 to R-19; A-1 to D-18; A-1 to V-17; A1 to H-16; A-1 to R-15; A1 to Y-14; A-1 to T-13; A-1 to G-12; A-1 to I-11; A-1 to L-10; A-1 to N-9; A-1 to S-8; A-1 to A-7; A-1 to K-6; of SEQ ID NO:2. Polynucleotides encoding these polypeptides are also encompassed by the invention.

Further embodiments of the invention are directed to polypeptide fragments comprising, or alternatively, consisting of, amino acids described by the general formula m to n, where m and n correspond to any one of the amino acid residues specified above for these symbols, respectively. Polynucleotides encoding these polypeptides are also encompassed by the invention.

Polypeptide fragments of the present invention include polypeptides comprising an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A–D (SEQ ID NO:1) or the complementary strand thereto. Protein fragments may be "freestanding," or comprised within a larger polypeptide of which the fragment forms a part or region, most preferably as a single continuous region. Representative examples of polypeptide fragments of the invention, include, for example, fragments that comprise or alternatively, consist of, from about amino acid residues −40 to 1, 1 to 20, 21 to 40, 41 to 60, 61 to 83, 84 to 100, 101 to 120, 121 to 140, 141 to 160, 160–167, 161 to 180, 181 to 200, 201 to 220, 221 to 240, 241 to 260, 261 to 280, 281 to 310, 311 to 350, 351 to 400, 401 to 450, 451 to 500, 551 to 600, or 601 to the end of the coding region of SEQ ID NO:2. Moreover, polypeptide fragments can be at least about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Among the especially preferred fragments of the invention are fragments characterized by structural or functional attributes of TR9. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of TR9. Certain preferred regions are those disclosed in FIG. 3 and include, but are not limited to, regions of the aforementioned types identified by analysis of the amino acid sequence depicted in FIGS. 1A–D, such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In specific embodiments, polypeptide fragments of the invention comprise, or alternatively, consist of, amino acid residues: 40 to 48, 40 to 51, 51 to 66, 66 to 73, 73 to 83, 83 to 104, 104 to 110, 110 to 128, 128 to 146, 146 to 152, 40 to 152, and/or 28 to 171 in SEQ ID NO:2.

In other embodiments, the fragments or polypeptides of the invention (i.e., those described herein) are not larger than. 610, 600, 580, 570, 550, 525, 500, 475, 450, 400, 425, 390, 380, 375, 350, 336, 334, 331, 305, 300, 295, 290, 285, 280, 275, 260, 250,225,200, 185, 175, 170, 165, 160, 155, 150, 145, 140, 135, 130, 125, 120, 115, 110, 105, 100, 90, 80, 75, 60, 50, 40, 30, or 25 amino acid residues in length.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate TR9 receptor-specific antibodies include: a polypeptide comprising amino acid residues from about 4 to about 81 in SEQ ID NO:2, about 116 to about 271 in SEQ ID NO:2, about 283 to about 308 in SEQ ID NO:2, about 336 to about 372 in SEQ ID NO:2, about 393 to about 434 in SEQ ID NO:2, about 445 to about 559 in SEQ ID NO:2, and about 571 to about 588 in SEQ ID NO:2. As indicated above, the inventors have determined that the above polypeptide fragments are antigenic regions of the TR9 receptor protein.

The epitope-bearing peptides and polypeptides of the invention may be produced by any conventional means. R. A. Houghten, "General Method for the Rapid Solid-Phase Synthesis of Large Numbers of Peptides: Specificity of Antigen-Antibody Interaction at the Level of Individual Amino Acids," *Proc. Natl. Acad Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, TR9 receptor polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TR9 protein or protein fragment alone (Fountoulakis et al., *J. Biochem.* 270:3958–3964 (1995)).

Polypeptide Assays

The present invention also relates to diagnostic assays such as quantitative and diagnostic assays for detecting levels of TR9 receptor protein, or the soluble form thereof, in cells and tissues, including determination of normal and abnormal levels. Thus, for instance, a diagnostic assay in accordance with the invention for detecting over-expression of TR9, or soluble form thereof, compared to normal control tissue samples may be used to detect the presence of tumors, for example. Assay techniques that can be used to determine levels of a protein, such as a TR9 protein of the present invention, or a soluble form thereof, in a sample derived from a host are well-known to those of skill in the art. Such assay methods include radioimmunoassays, competitive-binding assays, Western Blot analysis and ELISA assays.

Assaying TR9 protein levels in a biological sample can occur using any art-known method. By,. "biological sample" is intended any biological sample obtained from an individual, cell line, tissue culture, or other source which contains TR9 receptor protein or mRNA. Preferred for assaying TR9 protein levels in a biological sample are antibody-based techniques. For example, TR9 protein expression in tissues can be studied with classical immuno-histological methods. (Jalkanen et al., *J. Cell. Biol.* 101:976–985 (1985); Jalkanen et al., *J. Cell. Biol.* 105:3087–3096 (1987)). Other antibody-based methods useful for detecting TR9 receptor gene expression include immunoassays, such as the enzyme linked immunosorbent assay (ELISA) and the radioimmunoassay (RIA).

Suitable labels are known in the art and include enzyme labels, such as, glucose oxidase, and radioisotopes, such as iodine ($^{125}I$, $^{121}I$), carbon ($^{14}C$), sulphur ($^{35}S$), tritium ($^{3}H$), indium ($^{112}In$), and technetium ($^{99m}Tc$), and fluorescent labels, such as fluorescein and rhodamine, and biotin.

Therapeutics

The tumor necrosis factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," Symp. Quant. Biol. 51:597–609 (1986), Cold Spring Harbor; B. Beutler and A. Cerami, Annu. Rev. Biochem. 57:505–518 (1988); L. J. Old, Sci. Am. 258:59–75 (1988); W. Fiers, FEBS Lett. 285:199–224 (1991)). The TNF-family ligands induce such various cellular responses by binding to TNF-family receptors, including the TR9 of the present invention. Cells which express the TR9 polypeptide and are believed to have a potent cellular response to TR9 ligands include fetal liver, PBL, lung, kidney, small intestine, colon, keratinocytes, endothelial cells, and monocyte activated tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (J. C. Ameisen, AIDS 8:1197–1213 (1994); P. H. Krammer et al., Curr. Opin. Immunol. 6:279–289 (1994)).

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses the TR9 polypeptide, an effective amount of TR9 ligand, analog or an agonist capable of increasing TR9 mediated signaling. Preferably, TR9 mediated signaling is increased to treat a disease wherein decreased apoptosis or decreased cytokine and adhesion molecule expression is exhibited. Agonists include, but are not limited to, soluble forms of TR9 and antibodies (preferably monoclonal) directed against the TR9 polypeptide.

In a further aspect, the present invention is directed to a method for inhibiting apoptosis induced by a TNF-family ligand, which involves administering to a cell which expresses the TR9 polypeptide an effective amount of an antagonist capable of decreasing TR9 mediated signaling. Preferably, TR9 mediated signaling is decreased to treat a disease wherein increased apoptosis. NFkB expression and/or JNK expression is exhibited. Antagonists include, but are not limited to, soluble forms of TR9 polypeptide and antibodies (preferably monoclonal) directed against the TR9 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in Science 246:181–296 (1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique well known in the art involves expressing in cells a construct wherein the receptor is linked to a phospholipase C or D. Exemplary cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR9 receptors are contacted with ligands in the extracellular medium after they are secreted. A determination is then made as to whether the secreted protein will bind to TR9 receptor ligands.

Further screening assays for agonists and antagonists of the present invention are described in Tartaglia et al., *J. Biol. Chem.* 267:4304–4307(1992).

Thus, in a further aspect, a screening method is provided for determining whether a candidate agonist or antagonist is capable of enhancing or inhibiting a cellular response to a TNF-family ligand. The method involves contacting cells which express the TR9 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TR9 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonists include polyclonal and monoclonal antibodies raised against the TR9 polypeptides of the invention, or a fragment thereof. Such agonist antibodies raised against a TNF-family receptor are disclosed in Tartaglia et al., *Proc. Natl. Acad. Sci. USA* 88:9292–9296 (1991); and Tartaglia et al., *J. Biol. Chem.* 267:4304–4307(1992). See, also, PCT Application WO 94/09137.

Antagonists according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and -Hexachlorocyclohexane).

In specific embodiments, antagonists according to the present invention are nucleic acids corresponding to the sequences contained in FIGS. 1A–D, or the complementary strand thereof, and/or to nucleotide sequences contained in the deposited clone. In one embodiment, antisense sequence is generated internally by the organism, in another embodiment, the antisense sequence is separately administered (see, for example, O'Connor, J., *Neurochem.* 56:560 (1991). *Oligodeoxynucleotides as Antisense Inhibitors of Gene Expression*, CRC Press, Boca Raton, Fla. (1988). Antisense technology can be used to control gene expression through antisense DNA or RNA, or through triple-helix formation. Antisense techniques are discussed for example, in Okano, J., *Neurochem.* 56:560 (1991); *Oligodeoxynucleotides as Antisense Inhibitors of Gene Expression*, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA polynucleotide of from about 10 to 40 base pairs in length. A DNA polynucleotide is designed to be complementary to a region of the gene involved in transcription thereby preventing transcription and the production of the receptor. The antisense RNA polypeptide hybridizes to the mRNA in vivo and blocks translation of the mRNA molecule into receptor polypeptide. The polynucleotides described herein can also be delivered to cells such that the antisense RNA or DNA may be expressed in vivo to inhibit production of the receptor.

In one embodiment, the TR9 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR9 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TR9, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster et al., *Nature* 296:39–42 (1982)), etc.

The antisense nucleic acids of the invention comprise a sequence complementary to at least a portion of an RNA transcript of a TR9 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR9 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR9 RNA it may contain and still form a stable duplex (or triplex as the case may be). One skilled in the art can ascertain a tolerable degree of mismatch by use of standard procedures to determine the melting point of the hybridized complex.

Potential antagonists according to the invention also include catalytic RNA, or a ribozyme (See, e.g., PCT International Publication WO 90/11364, published Oct. 4, 1990; Sarver et al, *Science* 247:1222–1225 (1990). While ribozymes that cleave mRNA at site specific recognition sequences can be used to destroy TR9 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TR9 (FIGS. 1A–D). Preferably, the ribozyme is engineered so that the cleavage recognition site is located near the 5' end of the TR9 mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Further antagonists according to the present invention include soluble forms of TR9, (e.g., fragments of the TR9 receptor sequence depicted in FIGS. 1A–D that include the ligand binding domain from the extracellular region of the full length receptor). Such soluble forms of the receptor, which may be naturally occurring or synthetic, antagonize TR9 mediated signaling by competing with the cell surface TR9 for binding to TNF-family ligands. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes and Crispe, *J. Exp. Med.* 182:1395–1401 (1995)).

The experiments set forth in Example 5 and 6, indicate that the TR9 receptor, like other homologous proteins, is a death domain-containing molecule capable of triggering apoptosis, which is important in the regulation of the immune system. In addition, the experiments set forth below suggest that TR9-induced apoptosis will be blocked by the inhibitors of ICE-like proteases, CrmA and z-VAD-fmk. Importantly, it is also expected that apoptosis induced by TR9 will be blocked by dominant negative versions of FADD (FADD-DN) or FLICE (FLICE-DN/MACHα1C360S), which were previously shown to inhibit death signaling by Fas/APO-1 and TNFR-1. Thus, inhibitors of ICE-like proteases, FADD-DN and FLICE-DN/MACHα1C360S could also be used as antagonists for TR9 activity.

Antagonists of the present invention also include antibodies specific for TNF-family ligands or the TR9 polypeptides of the invention. The term "antibody" (Ab) or "monoclonal antibody" (mAb) as used herein is meant to include intact molecules as well as fragments thereof (such as, e.g., Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of standard methods using TR9 immunogens of the present invention. As indicated, such TR9 immunogens include the full length TR9 polypeptide depicted in FIGS. 1A–D (SEQ ID NO:2) (which may or may not include the leader sequence) and TR9 polypeptide fragments comprising, for example, the ligand binding domain, extracellular domain, transmembrane domain, intracellular domain, death domain, incomplete death domain, or any combination thereof.

Polyclonal and monoclonal antibody agonists or antagonists according to the present invention can be raised according to the methods disclosed in Tartaglia and Goeddel, *J. Biol. Chem.* 267(7):4304–4307(1992)); Tartaglia et al., *Cell* 73:213–216 (1993)), and PCT Application WO 94/09137 and are preferably specific to (i.e., bind uniquely to polypeptides of the invention having the amino acid sequence of SEQ ID NO:2. The term "antibody" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fc fragment intact antibody, clear more rapidly from the circulation, and may have less non-specific tissue binding of an intact antibody (Wahl et al., *J. Nucl. Med.*, 24:316–325 (1983)).

In a preferred method, antibodies according to the present invention are mAbs. Such mAbs can be prepared using hybridoma technology (Kohler and Millstein, *Nature* 256:495–497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the TR9 domains are also candidate agonists and antagonists according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (Gyuris, *Cell* 75:791–803 (1993); Zervos et al., *Cell* 72:223–232 (1993)). Preferably, the yeast two-hybrid system is used according to the present invention to capture compounds which bind to the ligand binding domain, extracellular, intracellular, transmembrane, and death domain of the TR9. Such compounds are good candidate agonists and antagonists of the present invention.

Using the two-hybrid assay described above, the intracellular domain of the TR9 receptor, or a portion thereof, may be used to identify cellular proteins which interact with the receptor in vivo. Such an assay may also be used to identify ligands with potential agonistic or antagonistic activity of TR9 receptor function. This screening assay has previously been used to identify protein which interact with the cytoplasmic domain of the murine TNF-RII and led to the identification of two receptor associated proteins. Rothe et al., *Cell* 78:681 (1994). Such proteins and amino acid sequences which bind to the cytoplasmic domain of the TR9 receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science*, 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to TR9 ligands including TRAIL, TNF-α, lymphotoxin-α (LT-α, also known as TNF-β), LT-β (found in complex heterotrimer LT-α2-β), FasL, CD40, CD27, CD30, 4-1BB, OX40, and nerve growth factor (NGF).

Representative therapeutic applications of the present invention are discussed in-more detail below. The state of immunodeficiency that defines AIDS is secondary to a decrease in the number and function of $CD4^+$ T-lymphocytes. Recent reports estimate the daily loss of $CD4^+$ T cells to be between $3.5 \times 10^7$ and $2 \times 10^9$ cells (Wei et al., Nature 373:117–122 (1995)). One cause of $CD4^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., AIDS 8:1197–1213 (1994); Finkel and Banda, Curr. Opin. Immunol. 6:605–615(1995); Muro-Cacho et al., J. Immunol. 154:5555–5566 (1995)). Furthermore, apoptosis and $CD4^+$ T-lymphocyte depletion is tightly correlated in different animal models of AIDS (Brunner et al., Nature 373:441–444 (1995); Gougeon et al., AIDS Res. Hum. Retroviruses 9:553–563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley et al., J. Virol. 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating $HIV^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way than, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence, the immune system is already at the effector stage. Agonists of the present invention are able to suppress the immune response to both allografts and xenografts because lymphocytes activated and differentiated into effector cells will express the TR9 polypeptide, and thereby are susceptible to compounds which enhance apoptosis. Thus, the present invention further provides a method for creating immune privileged tissues.

TR9 antagonists of the invention can further be used in the treatment of inflammatory diseases and stress response related diseases, such as inflammatory bowel disease, rheumatoid arthritis, osteoarthritis, psoriasis, and septicemia.

In addition, due to lymphoblast expression of TR9, soluble TR9 agonist or antagonist antibodies (e.g., mABs) may be used to treat this form of cancer. Further, soluble TR9 or neutralizing mABs may be used to treat various chronic and acute forms of inflammation such as rheumatoid arthritis, osteoarthritis, psoriasis, septicemia, and inflammatory bowel disease.

Modes of Administration The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR9 mediated apoptosis. Of course, where it is desired for apoptosis to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients (i.e., carriers).

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of TR9 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR9 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist (including TR9 receptor polynucleotides, polypeptides or antibodies of the invention) or agonist (e.g., TR9 polynucleotides, polypeptides of the invention or antibodies thereto) of TR9 and a pharmaceutically acceptable carrier or excipient, which may be administered orally, rectally, parenterally, intracistemally, intravaginally, intraperitoneally, topically (as by powders, ointments, drops or transdermal patch), bucally, or as an oral or nasal spray, In one embodiment "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions.

The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble TR9 polypeptides, TR9 polypeptides containing the transmembrane region can also be used when appropriately solubilized by including detergents, such as CHAPS or NP-40, with buffer.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a TR9 receptor gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3. untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, N.Y. (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of the TR9 Receptor in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6× His tag") covalently linked to the carboxyl terminus of that polypeptide. However, in this example, the polypeptide coding sequence is inserted such that translation of the six His codons is prevented and, therefore, the polypeptide is produced with no 6× His tag.

The DNA sequence encoding the desired portion of the TR9 receptor protein lacking the hydrophobic leader sequence is amplified from the deposited cDNA clone using PCR oligonucleotide primers which anneal to the amino terminal sequences of the desired portion of the TR9 receptor protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence:

5' CGC<u>CCATGG</u>CTCAGCCAGAACAGAAG 3' (SEQ ID NO:11) containing the underlined NcoI restriction site followed by 17 nucleotides complementary to the amino terminal coding sequence of the mature TR9 receptor sequence in FIGS. 1A–D. One of ordinary skill in the art would appreciate, of course, that the point in the protein coding sequence where the 5' primer begins may be varied to amplify a desired portion of the complete protein shorter or longer than the mature form. The 3' primer has the sequence:

5' CGC<u>AAGCTT</u>TTAGGGCAAATGCTCATTG3' (SEQ ID NO:12) containing the underlined HindIII restriction site followed by 19 nucleotides complementary to the 3' end of the non-coding sequence in the TR9 receptor DNA sequence in FIGS. 1A–D.

The amplified TR9 receptor DNA fragments and the vector pQE60 are digested with NcoI and HindIII, and the digested DNAs are then ligated together. Insertion of the TR9 receptor DNA into the restricted pQE60 vector places the TR9 receptor protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing TR9 receptor protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the TR9 receptor is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure TR9 receptor protein. The purified protein is stored at 4° C. or frozen at −80° C.

Example 2

Cloning and Expression of the TR9 Receptor Protein in a Baculovirus Expression System In this illustrative example, the plasmid shuttle vector pA2 is used to insert the cloned DNA encoding the complete protein, including its naturally associated secretary signal (leader) sequence, into a baculovirus to express the mature TR9 receptor protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length TR9 protein in the deposited clone, including the AUG initiation codon and the naturally associated leader sequence shown in FIGS. 1A–D (SEQ ID NO:2), is amplified using PCR oligonucleotide primers corresponding to the 5' and 3' sequences of the gene. The 5' primer has the sequence:

5' CGC<u>CCCGGG</u>GCCATCATGGGGACCTCTCCGAGC 3' (SEQ ID NO:13) containing the underlined SmaI restriction enzyme site, an efficient signal for initiation of translation in eukaryotic cells, as described by Kozak, M., *J. Mol. Biol.* 196:947–950 (1987), followed by a number of bases of the sequence of the complete TR9 receptor protein shown in FIGS. 1A–D, beginning with the AUG initiation codon.

The 3' primer (for cloning the soluble form) has the sequence:

5' CGC<u>GGTACC</u>TTAGGGCAAATGCTCATTG 3' (SEQ ID NO:14) containing the underlined Asp718 restriction site followed by nucleotides complementary to the 3' noncoding sequence in FIGS. 1A–D.

The amplified fragment is isolated from a 1% agarose gel using a commercially available kit ("Geneclean," BIO 101 Inc., La Jolla, Calif.). The fragment then is digested with SmaI and Asp718 and again is purified on a 1% agarose gel. This fragment is designated herein "F1".

The plasmid is digested with the restriction enzymes SmaI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human TR9 receptor gene using the PCR method, in which one of the primers that is used to amplify the gene and the second primer is from well within the vector so that only those bacterial colonies containing the TR9 receptor gene fragment will show amplification of the DNA. The sequence of the cloned fragment is confirmed by DNA sequencing. This plasmid is designated herein pBacTR9.

Five µg of the plasmid pBacTR9 are co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). One µg of BaculoGold™ virus DNA and 5 µg of the plasmid pBacTR9 are mixed in a sterile well of a microtiter plate containing 50 µl of serum-free Grace's medium (Life Technologies Inc., Rockville, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Rockville, Md.) is used to allow easy identification and isolation of gal-expressing clones, which produce bluestained plaques. (A detailed description of a "plaque assay" of this type can also be found in the user's guide for insect cell culture and baculovirology distributed by Life Technologies Inc., Rockville, Md., page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR9.

To verify the expression of the V-TR9 gene, Sf9 cells are grown in Grace's medium supplemented with 10% heat inactivated FBS. The cells are infected with the recombinant baculovirus V-TR9 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of TR9 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C 127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molec. Cell. Biol. 5:438–447 (1985)) plus a fragment of the CMV-enhancer (Boshart et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTR9-HA, is made by cloning a cDNA encoding TR9 into the expression vector pcDNAI/Amp or pcDNAIII (which can be obtained from Invitrogen, Inc.).

The expression vector pcDNAI/Amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37.767–778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the TR9 is cloned into the polylinker region of the vector so that recombinant protein expression is directed by the CMV promoter. The plasmid construction strategy is as follows. The TR9 cDNA of the deposited clone is amplified using primers that contain convenient restriction sites, much as described above for construction of vectors for expression of TR9 in *E. coli*. Suitable primers include the following, which are used in this example.

The 5' primer, containing the underlined SmaI site, a Kozak sequence, an AUG start codon and codons of the 5' coding region of the complete TR9 receptor has the following sequence: 5' CGC CCCGGGGCCATCATGGGGACCTCTCCGAGC 3' (SEQ ID NO:13).

The 3' primer, containing the underlined XbaI site, a stop codon, and nucleotides of the 3' coding sequence, has the following sequence (at the 3' end): 5' CGC TCTAGATCAAGCGTAGTCTGGGACGTCGTATGGG TAGGGCAAAT GCTCATTG3' (SEQ ID NO:15).

The PCR amplified DNA fragment and the vector, pcDNAI/Amp, are digested with SmaI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR9-encoding fragment.

For expression of recombinant TR9, COS cells are transfected with an expression vector, as described above, using DEAE-DEXTRAN, as described, for instance, in Sambrook et al. *Molecular Cloning: a Laboratory Manual*, Cold Spring Laboratory Press, Cold Spring Harbor, N.Y. (1989). Cells are incubated under conditions for expression of TR9 by the vector.

Expression of the TR9-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TR9 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies, Rockville, Md.) supplemented with the chemotherapeutic agent methotrexate. The amplification of the DHFR genes in cells resistant to methotrexate (MTX) has been well documented (see, e.g., Alt et al., *J. Biol Chem.* 253:1357–1370 (1978); Hamlin et. al., *Biochem. et Biophys. Acta*, 1097:107–143 (1990); and Page et. al., *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TR9 in a regulated way in mammalian cells (Gossen et. al., *Proc. Natl. Acad. Sci. USA* 89:5547–5551 (1992). For the polyadenylation of the mRNA other signals, e.g., from the human growth hormone or globin genes can be used as well; Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes SmaI and Asp718 and then dephosphorylated using calf intestinal phosphatase by procedures known in the art. The vector is then isolated from a 1% agarose gel.

The DNA sequence encoding the complete TR9 protein including its leader sequence is amplified using PCR oligonucleotide primers corresponding to the 5' and 3' sequences of the gene.

The 5' primer has the sequence:
5' CGCCCCGGGGCCATCATGGGGACCTCTCCGAGC 3' (SEQ ID NO:13) restriction enzyme site, an efficient signal for initiation of translation in eukaryotic cells, as described by Kozak, M., *J. Mol. Biol.* 196:947–950 (1987), followed by a number of bases of the coding sequence of the TR9 receptor protein shown in FIGS. 1A–D (SEQ ID NO:1).

The 3' primer (for cloning the soluble form) has the sequence:
5' CGCGGTACCTTAGGGCAAATGCTCATTG 3' (SEQ ID NO:14) containing the underlined Asp718 restriction site followed by nucleotides complementary to the non-translated region of the TR9 receptor gene shown in FIGS. 1A–D (SEQ ID NO:1).

The amplified fragment is digested with the endonucleases SmaI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 4

Tissue Distribution of TR9 mRNA Expression

Northern blot analysis is carried out to examine TR9 gene expression in human tissues, using methods described by, among others, Sambrook et al., supra. A cDNA probe containing the entire nucleotide sequence of the TR9 protein (SEQ ID NO: 1) is labeled with $^{32}$P using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe is then used to examine various human tissues for TR9 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Example 5

TR9 Induced Apoptosis

Overexpression of Fas/APO-1 and TNFR-1 in mammalian cells mimics receptor activation (M. Muzio et al., Cell 85:817–827 (1996); M. P. Boldin et al., Cell 85:803–815 (1996)). Thus, this system is utilized to study the functional role of TR9. Transient expression of TR9 in MCF7 breast carcinoma cells and 293 human embryonic kidney cells is investigated for induction of apoptosis.
Experimental Design
Cell death assays are performed essentially as previously described (A. M. Chinnaiyan et al., Cell 81:505–512 (1995); M. P. Boldin et al., J. Biol. Chem. 270: 7795–8 (1995); F. C. Kischkel et al., EMBO 14:5579–5588 (1995); A. M. Chinnaiyan et al., J. Biol. Chem. 271:4961–4965 (1996)). Briefly, MCF-7 human breast carcinoma clonal cell lines stably transfected with either vector alone, a CrmA expression construct (M. Tewari et al., J. Biol. Chem. 270:3255–60 (1995)), or FADD-DN expression construct (A. M. Chinnaiyan et al., J. Biol. Chem. 271:4961–4965 (1996)) are transiently transfected with pCMV-TR9-galatosidase in the presence of a ten-fold excess of pcDNA3 expression constructs encoding the indicated proteins using lipofectamine (GIBCO-BRL). 293 cells are likewise transfected using the CaPO4 method. The ICE family inhibitor z-VAD-fmk (Enzyme Systems Products, Dublin, Calif.) is added to the cells at a concentration of 10 M, 5 hrs after transfection. 32 hours following transfection, cells are fixed and stained with X-Gal as previously described (A. M. Chinnaiyan et al., Cell 81:505–12 (1995); M. P. Boldin et al., J. Biol. Chem. 270:7795–8 (1995); F. C. Kischkel et al., EMBO 14:5579–5588 (1995)).
Results The affected cells will display morphological alterations typical of cells undergoing apoptosis, becoming rounded, condensed, and detaching from the dish. Similar to TNFR-1 and Fas/APO-1 (M. Muzio et al., Cell 85:817–827 (1996); M. P. Boldin et al., Cell 85:803–815 (1996); M. Tewari et al., J. Biol. Chem. 270:3255–60 (1995)), TR9-induced apoptosis is blocked by the inhibitors of ICE-like proteases, CrmA and z-VAD-fmk.

Example 6

Characterization of TR9

Members of the TNF receptor family are crucial modulators of inflammatory and cellular immune responses, and mediate a variety of biological functions, ranging from cell proliferation, differentiation and apoptosis to cell survival (Nagata, S., Cell 88:355–365 (1997); Armitage, R. J., Curr. Opin. Immuno. 6:407–413 (1994); Golstein, P., Curr. Biol. 7:R750-R753 (1997); Baichwal et al., Curr. Biol. 7:R94–R96. (1997); Smith et al., Cell 76: 959–962 (1994); Anderson et al., Nature 390:175–179 (1997); and Cleveland et al., Cell 81:479–482 (1995)). This family of receptors is characterized by several extracellular, cysteine-rich motifs that compose the ligand binding domain (Armitage, R. J., Curr. Opin. Immuno. 6:407–413 (1994); and Smith et al., Cell 76: 959–962 (1994)). Upon ligation by their cognate ligands, these receptors engage a number of signal transduction pathways, including apoptosis, activation of NF κB and JNK pathways that modulate the expression of genes involved in the immune and stress response (Smith et al., Cell 76: 959–962 (1994)).

Within the TNF receptor family, six members have emerged as a distinct subgroup termed death receptors; they contain a cytoplasmic death domain and activation of these receptors leads to engagement of components of the cell death pathway (Nagata, S., Cell 88:355–365 (1997); and Golstein, P., Curr. Biol. 7:R750–R753 (1997)). Transmission of the death signal is mediated by a series of homophilic protein-protein interactions involving the death domain and death effector domain that was originally defined as being present in the adaptor molecule FADD/MORT1 and the death protease caspase-8 (Chinnaiyan et al., Semmin. Immunol. 9:66–67 (1997)). For example, when the death receptor CD95/Fas is ligated by cognate ligand or agonist antibody, the adaptor molecule FADD and the death protease caspase-8 are recruited to the signalling complex through interactions involving death and death effector domains, respectively (Chinnaiyan et al., Semmin. Immunol. 9:66–67 (1997); Muzio et al., Cell 85: 817–827 (1996); and Boldin et al., Cell 85:803–815 (1996)). On approximation, caspase-8 undergoes an autoactivation, initiating activation of the downstream caspases, cleavage of death substrates and demise of the cell (Muzio et al, J. Biol. Chem. 273:2952–2956 (1997); Baringa, M., Science 280:32–34

(1998); Salvesen et al., *Cell* 91:443–446 (1997); and Martin et al., *Cell* 82: 349–352 (1995)). In. contrast to CD-95 that directly engages the FADD-caspase-8 pathway (Muzio et al., *Cell* 85: 817–827 (1996); Boldin et al., *Cell* 85:803–815 (1996); Chinnaiyan et al., *Cell* 81:505–512 (1995); and Boldin et al., *J. Biol. Chem.* 270:7795–7789 (1995)), both TNFR1 and DR3 utilize a primary adaptor molecule termed TRADD, around which assembles the FADD-caspase-8 pathway, an NF κB activating pathway involving the death domain-containing Ser/Thr kinase RIP and a JNK activating pathway that is mediated by the adaptor molecule TRAF2 (Hsu et al., *Cell* 81:495–504 (1995); Hsu et al., *Immunity* 4:387–396 (1996); Chinnaiyan et al., *Science* 274:990–992 (1996); Kitson et al., *Nature* 384:372–375 (1996); Yeh et al., *Immunity* 7:715–725 (1997); Lee et al., *Immunity* 7:703–713 (1997); and Kelliher et al., *Immunity* 8:297–303 (1998). Finally, there exists a subsidiary death pathway involving the death domain-containing adaptor RAIDD that binds to caspase-2 and has been shown to be part of the TNFR1 receptor complex, although the exact physiologic relevance of this redundant pathway remains unclear (Duan et al., *Nature* 385:86–89 (1997); and Ahmad et al., *Cancer Res.* 57:615–619 (1997).

Here, we report the identification and initial characterization of TR9, a new member of the TNF receptor family possessing a cytoplasmic death domain. TR9 induced apoptosis in mammalian cells and was capable of engaging the NF κB and JNK pathways.

Materials and Methods

Expression Constructs—TR9 (amino acid residues 42–655 as dipicted in FIGS. 1A–D; amino acid residues 2–615 as presented in SEQ ID NO:2) and TR9 delta (amino acid residues 42–460 as dipicted in FIGS. 1A–D; amino acid residues 2–420 as presented in SEQ ID NO:2) were cloned into pCMV1FLAG (IBI-Kodak) as in frame fusions to a TR9-terminal Preprotrypsin leader sequence and FLAG tag encoded by the vector. cDNAs were obtained by polymerase chain reaction using DNA oligo primers for TR9: 5'-GGA AGATCTGCCAGAACAGAAGGCCTCGAAT-3' (SEQ ID NO:16) and 5'-CCATCTTCCTGACCTGCTGTAGTCTAGAGCC-3' (SEQ ID NO:17) and for TR9 delta: 5'-GGA AGATCTGCCAGAACAGAAGGCCTC GAAT-3' (SEQ ID NO:16) and 5'-GCCGACCACGAGCGGGCCTAG TCTAGAGCC-3' (SEQ ID NO:18). Constructs encoding DR4, FADD, CD95, DR3, TRADD, ICH1-pro, RAIDD and RIP have been described previously (Chinnaiyan et al., *Cell* 81:505–512 (1995); Hsu et al., *Cell* 81:495–504 (1995); Hsu et al., *Immunity* 4:387–396 (1996); Chinnaiyan et al., *Science* 274:990–992 (1996); Kelliher et al., *Immunity* 8:297–303 (1998); and Pan et al., *Science* 276:111–113 (1997)).

Apoptosis Assay—Cell death assays were performed as previously described (Chinnaiyan et al., *Cell* 81:505–512 (1995); and Pan et al., *Science* 276:111–113 (1997)). Both Hela and MCF7 cells were transfected using the lipofectamine procedure (Life Technologies, Inc.) according to the manufacturer's instructions.

Co-immunoprecipitation Assay—In vivo interaction assays have been described elsewhere (Chinnaiyan et al., *Cell* 81:505–512 (1995); and Pan et al., *Science* 276:111–113 (1997)). 293 cells were co-transfected with FLAG-TR9, FLAG-TR9 delta, FLAG-CD95, FLAG-DR3, FLAG-TNFR1, and ICH-1pro-FLAG, expression constructs using standard calcium phosphate precipitation. After transfection (at 38–40 hours), cell lysates were prepared and the FLAG-tagged expressed proteins were immunoprecipitated with FLAG M2 affinity gel (IBI-Kodak) and the presence of FADD, myc-tagged TRADD and RIP (myc-TRADD and myc-RIP), or RAIDD detected by immunoblotting with polyclonal antibody to FADD horseradish peroxidase (HRP)-conjugated antibody to myc (BMB), or polyclonal antibody to RAIDD.

NF-κB Luciferase Assay—NF κB luciferase assays were done as described elsewhere (Chinnaiyan et al., *Cell* 81:505–512 (1995); and Pan et al., *Science* 276:111–113 (1997)).

JNK Activation Assay—293 cells were cultured in MEM containing 10% FBS. Cells were plated in 6-well plates and transfected with TR9 expressing plasmid or vector alone at 60–70% confluency by the lipofectamine method according to the manufacturer's instructions. Forty hours post transfection, cell extracts were prepared in lysis buffer containing 20 mM HEPES, pH 7.4, 2 mM EDTA, 250 mM NaCl, 0.1% NP-40, 2 µg/ml leupeptin, 2 µg/ml aprotinin, 1 mM PMSF, 0.5 µg/ml benzamide, 1 mM DTT and 1 mM orthovanadate. The C-jun kinase assay was performed by a modified method as described (Haridas et al., *Immunol.* 160:3152–3162 (1998)). Briefly, cell extracts (70 µg) were subjected to immunoprecipitation with 0.03 µg anti-JNK antibody for 30 min at 4° C. Immuno-complexes were collected by incubation with protein A/G-sepharose beads for 30 min at 4° C. The beads were extensively washed with lysis buffer (4×400 µl) and kinase buffer (2×400 µl: 20 mM HEPES, pH 7.4, 1 mM DTT, 25 mM NaCl) and the kinase reaction allowed to proceed for 15 min at 30° C. with 2 µg GST-Jun (1–79) in 20 µl containing 20 mM HEPES, pH 7.4, 10 mM MgCl$_2$ 1 mM DTT and 10 µCi [γ$^{32}$P]ATP. Reactions were stopped by the addition of 15 µl SDS-sample buffer and resolved by SDS-polyacrylamide gel electrophoresis. GST-Jun (1–79) was visualized by staining with Coomassie Blue and the dried gel visualized following Phosphorimager analysis (Molecular Dynamics; Sunyvale, Calif.) and quantitation by ImageQuant Software (Molecular Dynamics). A specific assay for JNK activity involved the co-transfection of 3×10$^6$ 293 cells with vector, or the CD40, TR9, or TR9 delta expression constructs (6.4 µg) together with 2.4 µg of a JNK-myc expression plasmid using the calcium phosphate precipitation method. After transfection (approximately 36 hours), cell extracts were prepared by lysis in NP 40 buffer (20 mM Tris-Cl, pH 8.0, 137 mM NaCl, 10% Glycerol, 2 mM EDTA, 5 mM Na$_2$VO$_4$, 0.5 mM PMSF and 1% NP40) plus protease inhibitor cocktail (BMB). Immunoprecipitation of JNK-myc was performed using monoclonal anti-myc antibody (10 µg, Babco) and immunocomplexes precipitated with 20 µl protein G-sepharose (50% slurry, Sigma) and detected by blotting with anti-myc-HRP. FLAG tagged CD40, TR9, and TR9 delta were immunoprecipitated with anti-FLAG M2 affinity gel and detected by blotting with anti-FLAG antibody. The kinase assay utilized 2 µg GST Jun(1–79) as substrate, 50 mM ATP and 5 µCi γ$^{32}$P]ATP in 30 µl kinase buffer (30 mM HEPES, pH 7.4, 7 mM Mn Cl$_2$, 5 mM MgCl$_2$ and 1 mM DTT).

Results and Discussion

TR9 has a putative signal sequence (amino acid residues 1–41 as depicted in FIGS. 1A–D and 4A; amino acid residues −40 to 1 in SEQ ID NO:2), with the mature form predicted to start at amino acids 42 (Gln) as depicted in FIGS. 1A–D and 4A (Nielson et al., *Protein. Eng.* 10:1–6 (1997)). The extracellular portion (amino acid residues 42–350 as depicted in FIGS. 1A–D and 4A; amino acid residues 2–310 in SEQ ID NO:2) contains four TNFR-like cysteine-rich motifs of TR9 (amino acid residues 67–211 as depicted in FIGS. 1A–D; amino acid residues 27–171 in SEQ ID NO:2) that are most related to those of osteoprotegerin (OPG) and TNFR2 with 36% and 42% amino acid identities, respectively (FIG. 4B; data not shown). A transmembrane domain (amino acids 351 to 370 as depicted in FIGS. 1A–D and 4A; residues 311 to 330 of SEQ ID NO:2) is followed by a 285-amino acid long cytoplasmic portion of the molecule that contains a death domain related to those of all known death receptors (FIG. 4C), being most related to the death domain of TNFR1 (27.2%) and least like that of DR5 (19.7%). Curiously, unlike other death receptors that have death domains present in their COOH-terminus, the death domain in TR9 was located adjacent to the transmembrane domain followed by a 150 amino acid tail. Interestingly, following the death domain was a putative leucine zipper sequence overlapping with a proline-rich region reminescent of a SH3 domain-binding motif (FIG. 4A) (Pawson et al., Science 278:2075–2080 (1997)).

TR9 mRNA expression in human tissues and cancer cell lines—A 4-kb TR9 transcript was found in most human adult tissue, immune tissue, and cancer cell lines represented on Northern blots (Clontech) that were probed with TR9 cDNA according to the manufacturers instructions (data not shown). The transcript was abundant in heart, brain, placenta, pancreas, lymph node, thymus and prostate. Lower levels were detected in lung, skeletal muscle, kidney, testis, uterus, small intestine, colon, spleen, bone marrow, and fetal liver. However, adult liver and peripheral blood leukocytes expressed little TR9 mRNA. Additionally, smaller transcripts of 3.1 and 2.4 kb were observed in the testis and fetal liver, respectively.

Among human cancer cell lines, abundant levels of 4-kb transcript was detected in several nonlymphoid tumor cells, including cervical carcinoma Hela S3, colorectal adenocarcinoma SW480, lung carcinoma A549, and melanoma G361 cells. Significantly, less or no expression was observed in lines of hematopoietic origin (e.g., Raji, K562, and HL-60; data not shown).

Figure 5:
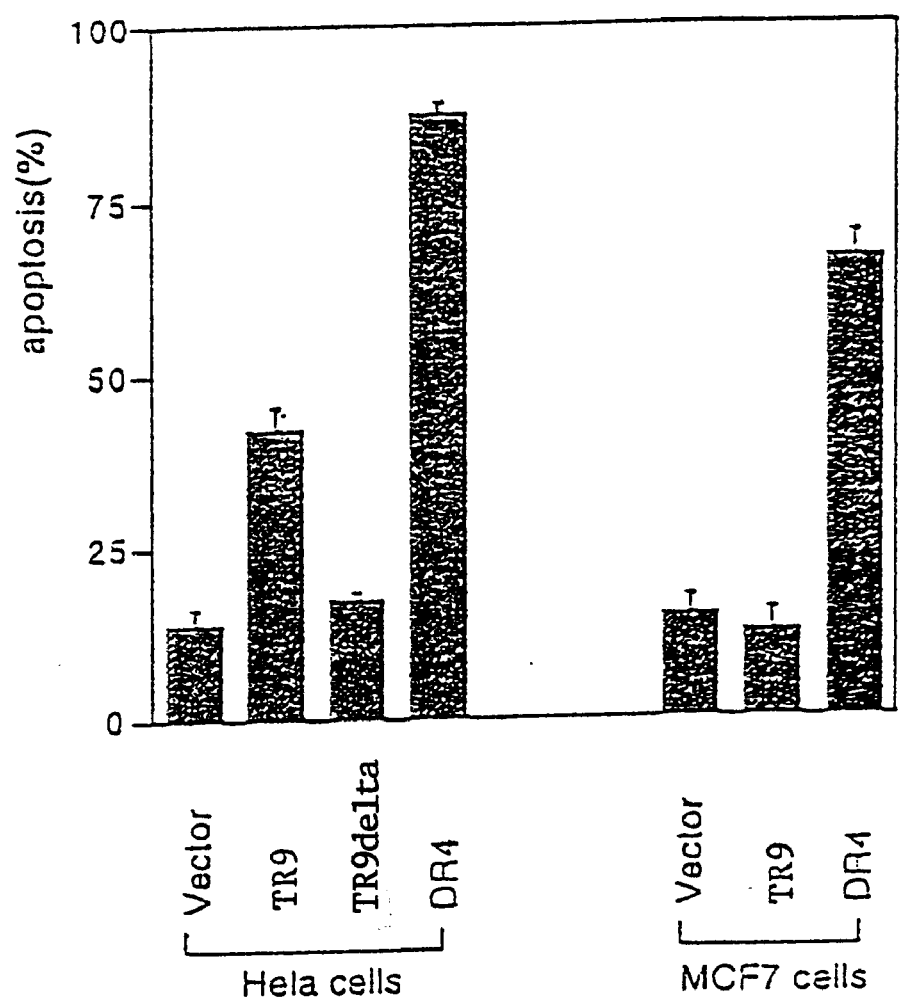
FIG. 5. TR9 induces apoptosis in mammalian cells. Ectopic expression of TR9 induces apoptosis in Hela cells, but not in MCF7 cells. Hela and MCF7 cells were cotransfected with a empty vector, TR9, TR9 delta, or DR4, together with a β-galactosidase-expressing reporter construct using a lipofectamine method according to the manufacturer's instructions (BRL). Nineteen hours after transfection, cells were stained with 5-bromo-4-chloro-3-indoxyl-β-D-galactopyranoside (X-Gal) and examined as described in Chinnaiyan et al., Cell 81:505–512 (1995). The data (mean±SD) represent the percentage of round, apoptotic cells as a function of total β-galactosidase-positive cells (n=4).

TR9 induces apoptosis in mammalian cells—Since ectopic expression of death receptors can induce cell death in a ligand-independent manner (Chinnaiyan et al., Cell 81:505–512 (1995); Boldin et al., J. Biol. Chem. 270:7795–7789 (1995); Chinnaiyan et al., Science 274:990–992 (1996); Kitson et al., Nature 384:372–375 (1996); and Pan et al., Science 276:111–113 (1997)), we tested if TR9 could induce apoptosis upon overexpression. When Hela S3 cervical carcinoma cells were transfected with a TR9-expressing construct, 43% of the transfected cells underwent morphological changes characteristic of apoptosis (FIG. 5). As expected, deletion of the putative death domain (TR9 delta) abolished its killing activity. Significantly, TR9 was unable to induce cell death in human breast carcinoma MCF7 cells although they were very sensitive to DR4 killing (FIG. 5 and not shown), suggesting that the cell death pathway engaged by TR9 may be distinct from that engaged by other death receptors. Alternatively, the apoptotic activity of TR9 may be modulated by other signaling pathways it activates (see below) or ligand binding may be required to unveil its full killing capacity.

Interaction of TR9 with adaptor molecules in vivo—Death receptors utilize the adaptor molecules FADD (for CD95) or both TRADD and FADD (for TNFR1 and DR3) to transmit the death signal (Chinnaiyan et al., Cell 81:505–512 (1995); Boldin et al., J. Biol. Chem. 270:7795–7789 (1995); Chinnaiyan et al., Science 274:990–992 (1996); and Kitson et al., Nature 384:372–375 (1996)). We thus determined if TR9 could bind any of these adaptor molecules in human embryonic kidney 293 cells. TR9 did not interact with FADD, although the association between CD95 and FADD was readily detected under similar conditions (data not shown). Interestingly, TR9 was found to associate with TRADD, although the interaction was weaker than that between DR3 and TRADD (data not shown). This observation is consistent with the observation that TR9 has a weaker killing ability. Alternatively, TR9 may use a TRADD-related molecule as an adaptor, or the observed association might be bridged by another adaptor protein. Interaction was not detectable between TR9 and RAIDD or RIP, two other adaptor molecules known to be recruited to the TNFR1 and DR3 signalling complexes (data not shown).

TR9 activates nuclear factor-κB—Both TNFR1 and DR3 can engage a signal transduction pathway that leads to the activation of NF-κB (Smith et al., Cell 76: 959–962 (1994); Chinnaiyan et al., Science 274:990–992 (1996); Kitson et al., Nature 384:372–375 (1996); and Baker et al., Oncogene 12:1–9 (1996)). The ability of TR9 to activate NF-κB was tested in a luciferase reporter assay and was found to induce NF-κB activation in a dose-dependent manner (FIG. 6). Presumably overexpressing the receptor allowed it to achieve an active configuration that was competent to signal the NF-κB system. Interestingly, the cytoplasmic deletion of TR9 that abolished its apoptotic activity similarly abrogated its ability to activate NF-κB (data not shown), suggesting that these two signaling pathways may be mediated by a common receptor-proximal adapter molecule.

Ectopic expression of TR9 induces JNK activation—JNK activation is known to be induced by several TNF receptors including TNFR1 and CD40 (Smith et al., Cell 76: 959–962 (1994); Yeh et al., Immunity 7:715–725 (1997); Lee et al., Immunity 7:703–713 (1997); and Baker et al., Oncogene 12:1–9 (1996)). We next determined whether overexpression of TR9 could lead to JNK activation using an in vitro kinase assay. TR9 was found to induce JNK activation in a dose-dependent manner (data not shown). The cytoplasmic truncation that attenuated cell death or NF-κB activation had surprisingly little effect on JNK activation (data not shown). This would be consistent with the notion that JNK activation is mediated by a cytoplasmic segment different from that responsible for apoptosis and NF-κB induction. It is noteworthy that two potential TRAF-binding motifs are present adjacent to the transmembrane domain PRQDP (amino acid residues 381–385 as depicted in FIGS. 1A–D; amino acid residues 341–345 as presented in SEQ ID NO:2), and PTQNR (amino acid residues 400–404 as depicted in FIGS. 1A–D; amino acid residues 360–364 as presented in SEQ ID NO:2) (Gedrich et al., J. Biol. Chem. 271:12852–12858 (1996) and Boucher et al., Biochem. and Biophy. Res. Communi. 233:592–600 (1997)).

In conclusion, we have identified a novel death domain-containing TNF receptor designated TR9. TR9 engages a cell death pathway different from those initiated by the CD95, TNFR1 or TRAIL/Apo2L receptors. In addition, TR9 also activates NF-κB and JNK, two signaling pathways shared by TNFR1. Thus, it is likely that like the other members of the TNF receptor family, TR9 plays a role in inflammatory responses and immune regulation.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a polynucleotide sequence selected from the group consisting of:

(a) a polynucleotide sequence encoding amino acid residues −40 to 615 of SEQ ID NO:2;

(b) a polynucleotide sequence encoding amino acid residues −39 to 615 of SEQ ID NO:2;

(c) a polynucleotide sequence encoding amino acid residues 1 to 615 of SEQ ID NO:2;

(d) a polynucleotide sequence encoding amino acid residues 1 to 310 of SEQ ID NO:2;

(e) a polynucleotide sequence encoding amino acid residues 27 to 171 of SEQ ID NO:2;

(f) a polynucleotide sequence encoding amino acid residues 328 to 615 of SEQ ID NO:2;

(g) a polynucleotide sequence encoding amino acid residues 389 to 455 of SEQ ID NO:2; and (h) a polynucleotide sequence complementary to any of the polynucleotide sequences in (a), (b), (c), (d), (e), (f) or (g), above over their entire length.

2. The isolated nucleic acid molecule of claim 1 which comprises polynucleotide sequence (a).

3. The isolated nucleic acid molecule of claim 1 which comprises polynucleotide sequence (b).

4. The isolated nucleic acid molecule of claim 1 which comprises polynucleotide sequence (c).

5. The isolated nucleic acid molecule of claim 1 which comprises polynucleotide sequence (d).

6. The isolated nucleic acid molecule of claim 1 which comprises polynucleotide sequence (e).

7. The isolated nucleic acid molecule of claim 1 which comprises polynucleotide sequence (f).

8. The isolated nucleic acid molecule of claim 1 which comprises polynucleotide sequence (g).

9. The isolated nucleic acid molecule of claim 1 which comprises polynucleotide sequence (h).

10. The isolated nucleic acid molecule of claim 1 which encodes a polypeptide which regulates cell death.

11. The isolated nucleic acid molecule of claim 1 wherein the polynucleotide sequence further comprises a heterologous polynucleotide sequence.

12. The isolated nucleic acid molecule of claim 11 wherein the heterologous polynucleotide sequence encodes a heterologous polypeptide.

13. The isolated nucleic acid molecule of claim 12 wherein the heterologous polypeptide is the Fc domain of immunoglobulin.

14. A recombinant vector comprising the isolated nucleic acid molecule of claim 1.

15. The recombinant vector of claim 14 wherein the nucleic acid molecule is operably associated with a heterologous regulatory sequence that controls gene expression.

16. An isolated recombinant host cell comprising the isolated nucleic acid molecule of claim 1.

17. The recombinant host cell of claim 16 wherein the nucleic acid molecule is operably associated with a heterologous regulatory sequence that controls gene expression.

18. A method for producing a polypeptide, comprising:
    (a) culturing a host cell under conditions suitable to produce a polypeptide encoded by the nucleic acid molecule (a), (b), (c), (d), (e), (f) or (g) of claim 1; and
    (b) recovering the polypeptide from the cell culture.

19. A composition comprising the nucleic acid of claim 1 and a pharmaceutically acceptable carrier.

20. An isolated nucleic acid molecule comprising a polynucleotide sequence selected from the group consisting of:
    (a) a polynucleotide sequence encoding the full-length polypeptide having the amino acid sequence encoded by the cDNA plasmid contained in ATCC Deposit No. 209037;
    (b) a polynucleotide sequence encoding the full-length polypeptide excluding the N-terminal methionine residue, having the amino acid sequence encoded by the cDNA plasmid contained in ATCC Deposit No. 209037;
    (c) a polynucleotide sequence encoding the extracellular domain of the polypeptide having the amino acid sequence encoded by the cDNA plasmid contained in ATCC Deposit No. 209037;
    (d) a polynucleotide sequence encoding the partial death domain of the polypeptide having the amino acid sequence encoded by the cDNA plasmid contained in ATCC Deposit No. 209037; and
    (e) a polynucleotide sequence encoding a fragment of the polypeptide having the amino acid sequence encoded by the cDNA plasmid contained in ATCC Deposit No. 209037 wherein said fragment regulates cell death.

21. The isolated nucleic acid molecule of claim 20 which comprises polynucleotide sequence (a).

22. The isolated nucleic acid molecule of claim 20 which comprises polynucleotide sequence (b).

23. The isolated nucleic acid molecule of claim 20 which comprises polynucleotide sequence (c).

24. The isolated nucleic acid molecule of claim 20 which comprises polynucleotide sequence (d).

25. The isolated nucleic acid molecule of claim 20 which comprises polynucleotide sequence (e).

26. The isolated nucleic acid molecule of claim 20 which encodes a polypeptide which regulates cell death.

27. The isolated nucleic acid molecule of claim 20 wherein the polynucleotide sequence further comprises a heterologous polynucleotide sequence.

28. The isolated nucleic acid molecule of claim 27 wherein the heterologous polynucleotide sequence encodes a heterologous polypeptide.

29. The isolated nucleic acid molecule of claim 28 wherein the heterologous polypeptide is the Fc domain of immunoglobulin.

30. A recombinant vector comprising the isolated nucleic acid molecule of claim 20.

31. The recombinant vector of claim 30 wherein the nucleic acid molecule is operably associated with a heterologous regulatory sequence that controls gene expression.

32. An isolated recombinant host cell comprising the isolated nucleic acid molecule of claim 20.

33. The recombinant host cell of claim 32 wherein the nucleic acid molecule is operably associated with a heterologous regulatory sequence that controls gene expression.

34. A method for producing a polypeptide, comprising:
    (a) culturing a host cell under conditions suitable to produce a polypeptide encoded by the nucleic acid molecule of claim 20; and
    (b) recovering the polypeptide from the cell culture.

35. A composition comprising the nucleic acid of claim 20 and a pharmaceutically acceptable carrier.

36. An isolated nucleic acid molecule consisting of polynucleotide sequence of at least 30 contiguous nucleotides of nucleotide position 500 to nucleotide position 980 of SEQ ID NO:1.

37. The isolated nucleic acid molecule of claim 36 consisting of polynucleotide sequence of at least 50 contiguous nucleotides of nucleotide position 500 to nucleotide position 980 of SEQ ID NO:1.

38. The isolated nucleic acid molecule of claim 36 which encodes a polypeptide which regulates cell death.

39. The isolated nucleic acid of claim 36 wherein the polynucleotide sequence further comprises a heterologous polynucleotide sequence.

40. The isolated nucleic acid of claim 39 wherein the heterologous polynucleotide sequence encodes a heterologous polypeptide.

41. The isolated nucleic acid molecule of claim 40 wherein the heterologous polypeptide is the Fc domain of immunoglobulin.

42. A recombinant vector comprising the isolated nucleic acid molecule of claim 36.

43. The recombinant vector of claim 42 wherein the nucleic acid molecule is operably associated with a heterologous regulatory sequence that controls gene expression.

44. An isolated recombinant host cell comprising the isolated nucleic acid molecule of claim 36.

45. The recombinant host cell of claim 44 wherein the nucleic acid molecule is operably associated with a heterologous regulatory sequence that controls gene expression.

46. A method for producing a polypeptide, comprising:
    (a) culturing a host cell under conditions suitable to produce a polypeptide encoded by the nucleic acid of claim 36; and
    (b) recovering the polypeptide from the cell culture.

47. A composition comprising the nucleic acid of claim 36 and a pharmaceutically acceptable carrier.

48. An isolated nucleic acid molecule consisting of a polynucleotide sequence encoding at least 30 contiguous amino acid residues of SEQ ID NO:2.

49. The isolated nucleic acid molecule of claim 48 consisting of a polynucleotide sequence which encodes at least 50 contiguous amino acid residues of SEQ ID NO:2.

50. The isolated nucleic acid molecule of claim 48 which encodes a polypeptide which regulates cell death.

51. The isolated nucleic acid of claim 48 wherein the polynucleotide sequence further comprises a heterologous polynucleotide sequence.

52. The isolated nucleic acid of claim 51 wherein the heterologous polynucleotide sequence encodes a heterologous polypeptide.

53. The isolated nucleic acid molecule of claim 52 wherein the heterologous polypeptide is the Fc domain of immunoglobulin.

54. A recombinant vector comprising the isolated nucleic acid molecule of claim 48.

55. The recombinant vector of claim 54 wherein the nucleic acid molecule is operably associated with a heterologous regulatory sequence that controls gene expression.

56. An isolated recombinant host cell comprising the isolated nucleic acid molecule of claim 48.

57. The recombinant host cell of claim 56 wherein the nucleic acid molecule is operably associated with a heterologous regulatory sequence that controls gene expression.

58. A method for producing a polypeptide, comprising:
   (a) culturing a host cell under conditions suitable to produce a polypeptide encoded by the nucleic acid of claim 48; and
   (b) recovering the polypeptide from the cell culture.

59. A composition comprising the nucleic acid of claim 48 and a pharmaceutically acceptable carrier.

60. An isolated nucleic acid molecule comprising a first polynucleotide sequence 90% or more identical to a second polynucleotide sequence selected from the group consisting of:
   (a) a polynucleotide sequence encoding amino acid residues −40 to 615 of SEQ ID NO:2;
   (b) a polynucleotide sequence encoding amino acid residues −39 to 615 of SEQ ID NO:2;
   (c) a polynucleotide sequence encoding amino acid residues 1 to 615 of SEQ ID NO:2;
   (d) a polynucleotide sequence encoding amino acid residues 1 to 310 of SEQ ID NO:2;
   (e) a polynucleotide sequence encoding amino acid residues 27 to 171 of SEQ ID NO:2;
   (f) a polynucleotide sequence encoding amino acid residues 328 to 615 of SEQ ID NO:2; and
   (g) a polynucleotide sequence encoding amino acid residues 389 to 455 of SEQ ID NO:2 wherein said first polynucleotide encodes a polypeptide which regulates cell death.

61. The isolated nucleic acid molecule of claim 60 wherein said second polynucleotide sequence is (a).

62. The isolated nucleic acid molecule of claim 60 wherein said second polynucleotide sequence is (b).

63. The isolated nucleic acid molecule of claim 60 wherein said second polynucleotide sequence is (c).

64. The isolated nucleic acid molecule of claim 60 wherein said second polynucleotide sequence is (d).

65. The isolated nucleic acid molecule of claim 60 wherein said second polynucleotide sequence is (e).

66. The isolated nucleic acid molecule of claim 60 wherein said second polynucleotide sequence is (f).

67. The isolated nucleic acid molecule of claim 60 wherein said second polynucleotide sequence is (g).

68. The isolated nucleic acid molecule of claim 60 wherein said first polynucleotide sequence is 95% or more identical to said second polynucleotide sequence.

69. The isolated nucleic acid molecule of claim 68 wherein said second polynucleotide sequence is a polynucleotide sequence encoding amino acid residues −40 to +615 of SEQ ID NO:2.

70. The isolated nucleic acid molecule of claim 68 wherein said second polynucleotide sequence is a polynucleotide sequence encoding amino acid residues −39 to +615 of SEQ ID NO:2.

71. The isolated nucleic acid molecule of claim 68 wherein said second polynucleotide sequence is a polynucleotide sequence encoding amino acid residues +1 to +615 of SEQ ID NO:2.

72. The isolated nucleic acid molecule of claim 68 wherein said second polynucleotide sequence is a polynucleotide sequence encoding amino acid residues +1 to 310 of SEQ ID NO:2.

73. The isolated nucleic acid molecule of claim 68 wherein said second polynucleotide sequence is a polynucleotide sequence encoding amino acid residues +27 to +171 of SEQ ID NO:2.

74. The isolated nucleic acid molecule of claim 68 wherein said second polynucleotide sequence is a polynucleotide sequence encoding amino acid residues +328 to +615 of SEQ ID NO:2.

75. The isolated nucleic acid molecule of claim 68 wherein said second polynucleotide sequence is a polynucleotide sequence encoding amino acid residues +389 to +455 of SEQ ID NO:2.

76. The isolated nucleic acid molecule of claim 60 which encodes a polypeptide which regulates cell death.

77. The isolated nucleic acid of claim 60 wherein the polynucleotide sequence further comprises a heterologous polynucleotide sequence.

78. The isolated nucleic acid of claim 77 wherein the heterologous polynucleotide sequence encodes a heterologous polypeptide.

79. The isolated nucleic acid molecule of claim 78 wherein the heterologous polypeptide is the Fc domain of immunoglobulin.

80. A recombinant vector comprising the isolated nucleic acid molecule of claim 68.

81. The recombinant vector of claim 80 wherein the nucleic acid molecule is operably associated with a heterologous regulatory sequence that controls gene expression.

82. An isolated recombinant host cell comprising the isolated nucleic acid molecule of claim 60.

83. The recombinant host cell of claim 82 wherein the nucleic acid molecule is operably associated with a heterologous regulatory sequence that controls gene expression.

84. A method for producing a polypeptide, comprising:
   (a) culturing a host cell under conditions suitable to produce a polypeptide encoded by the nucleic acid of claim 60; and
   (b) recovering the polypeptide from the cell culture.

85. A composition comprising the nucleic acid of claim 60 and a pharmaceutically acceptable carrier.

86. An isolated nucleic acid molecule comprising a polynucleotide sequence encoding a fragment of SEQ ID NO:2, wherein said fragment regulates cell death.

87. An isolated nucleic acid molecule comprising a polynucleotide sequence encoding a fragment of the amino acid sequence encoded by the cDNA plasmid contained in ATCC Deposit No. 209037, wherein said fragment regulates cell death.

88. An isolated polynucleotide wherein said polynucleotide comprises the nucleotide sequence contained in SEQ ID NO:1 encoding the TR9 polypeptide of SEQ ID NO:2.

* * * * *

UNITED STATES PATENT AND TRADEMARK OFFICE
CERTIFICATE OF CORRECTION

PATENT NO. : 6,949,358 B1
DATED : September 27, 2005
INVENTOR(S) : Ni et al.

It is certified that error appears in the above-identified patent and that said Letters Patent is hereby corrected as shown below:

Drawings, insert attached Figure 4C between Figures 4A-B and Figure 5.

Signed and Sealed this

Twenty-first Day of March, 2006

JON W. DUDAS
*Director of the United States Patent and Trademark Office*

Figure 4C

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 3474 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 247..2211

(ix) FEATURE:
      (A) NAME/KEY: mat_peptide
      (B) LOCATION: 367..2211

(ix) FEATURE:
      (A) NAME/KEY: sig_peptide
      (B) LOCATION: 247..364

(xi) SEQUENCE DESCRIPTION: SEQ ID NO:1:

```
GCGGGCTGCA GTCGCGGCGG CTTCTCCCCG CCTGGGCGGC CGCGCCGCTG GGCAGGTGCT      60

GAGCGCCCCT AGAGCCTCCC TTGCCGCCTC CCTCCTCTGC CCGGCCGCAG CAGTGCACAT     120

GGGGTGTTGG AGGTAGATGG GCTCCCGGCC CGGGAGGCGG CGGTGGATGC GGCGCTGGGC     180

AGAAGCAGCC GCCGATTCCA GCTGCCCCGC GCGCCCCGGG CGCCCCTGCG AGTCCCCGGT     240

TCAGCC ATG GGG ACC TCT CCG AGC AGC AGC ACC GCC CTC GCC TCC TGC        288
       Met Gly Thr Ser Pro Ser Ser Ser Thr Ala Leu Ala Ser Cys
       -40             -35                 -30

AGC CGC ATC GCC CGC CGA GCC ACA GCC ACG ATG ATC GCG GGC TCC CTT       336
Ser Arg Ile Ala Arg Arg Ala Thr Ala Thr Met Ile Ala Gly Ser Leu
-25                 -20                 -15

CTC CTG CTT GGA TTC CTT AGC ACC ACC ACA GCT CAG CCA GAA CAG AAG       384
Leu Leu Leu Gly Phe Leu Ser Thr Thr Thr Ala Gln Pro Glu Gln Lys
-10             -5                   1               5

GCC TCG AAT CTC ATT GGC ACA TAC CGC CAT GTT GAC CGT GCC ACC GGC       432
Ala Ser Asn Leu Ile Gly Thr Tyr Arg His Val Asp Arg Ala Thr Gly
            10                  15                  20

CAG GTG CTA ACC TGT GAC AAG TGT CCA GCA GGA ACC TAT GTC TCT GAG       480
Gln Val Leu Thr Cys Asp Lys Cys Pro Ala Gly Thr Tyr Val Ser Glu
        25                  30                  35

CAT TGT ACC AAC ACA AGC CTG CGC GTC TGC AGC AGT TGC CCT GTG GGG       528
His Cys Thr Asn Thr Ser Leu Arg Val Cys Ser Ser Cys Pro Val Gly
    40                  45                  50

ACC TTT ACC AGG CAT GAG AAT GGC ATA GAG AAA TGC CAT GAC TGT AGT       576
Thr Phe Thr Arg His Glu Asn Gly Ile Glu Lys Cys His Asp Cys Ser
55                  60                  65                  70

CAG CCA TGC CCA TGG CCA ATG ATT GAG AAA TTA CCT TGT GCT GCC TTG       624
Gln Pro Cys Pro Trp Pro Met Ile Glu Lys Leu Pro Cys Ala Ala Leu
                75                  80                  85

ACT GAC CGA GAA TGC ACT TGC CCA CCT GGC ATG TTC CAG TCT AAC GCT       672
Thr Asp Arg Glu Cys Thr Cys Pro Pro Gly Met Phe Gln Ser Asn Ala
            90                  95                 100

ACC TGT GCC CCC CAT ACG GTG TGT CCT GTG GGT TGG GGT GTG CGG AAG       720
Thr Cys Ala Pro His Thr Val Cys Pro Val Gly Trp Gly Val Arg Lys
        105                 110                 115
```

-continued

| | | |
|---|---|---|
| AAA GGG ACA GAG ACT GAG GAT GTG CGG TGT AAG CAG TGT GCT CGG GGT<br>Lys Gly Thr Glu Thr Glu Asp Val Arg Cys Lys Gln Cys Ala Arg Gly<br>120                       125                     130 | 768 |
| ACC TTC TCA GAT GTG CCT TCT AGT GTG ATG AAA TGC AAA GCA TAC ACA<br>Thr Phe Ser Asp Val Pro Ser Ser Val Met Lys Cys Lys Ala Tyr Thr<br>135                    140                  145                 150 | 816 |
| GAC TGT CTG AGT CAG AAC CTG GTG GTG ATC AAG CCG GGG ACC AAG GAG<br>Asp Cys Leu Ser Gln Asn Leu Val Val Ile Lys Pro Gly Thr Lys Glu<br>                  155                  160                  165 | 864 |
| ACA GAC AAC GTC TGT GGC ACA CTC CCG TCC TTC TCC AGC TCC ACC TCA<br>Thr Asp Asn Val Cys Gly Thr Leu Pro Ser Phe Ser Ser Ser Thr Ser<br>                  170                  175                  180 | 912 |
| CCT TCC CCT GGC ACA GCC ATC TTT CCA CGC CCT GAG CAC ATG GAA ACC<br>Pro Ser Pro Gly Thr Ala Ile Phe Pro Arg Pro Glu His Met Glu Thr<br>            185                  190                  195 | 960 |
| CAT GAA GTC CCT TCC TCC ACT TAT GTT CCC AAA GGC ATG AAC TCA ACA<br>His Glu Val Pro Ser Ser Thr Tyr Val Pro Lys Gly Met Asn Ser Thr<br>200                       205                     210 | 1008 |
| GAA TCC AAC TCT TCT GCC TCT GTT AGA CCA AAG GTA CTG AGT AGC ATC<br>Glu Ser Asn Ser Ser Ala Ser Val Arg Pro Lys Val Leu Ser Ser Ile<br>215                       220                  225                 230 | 1056 |
| CAG GAA GGG ACA GTC CCT GAC AAC ACA AGC TCA GCA AGG GGG AAG GAA<br>Gln Glu Gly Thr Val Pro Asp Asn Thr Ser Ser Ala Arg Gly Lys Glu<br>                  235                  240                  245 | 1104 |
| GAC GTG AAC AAG ACC CTC CCA AAC CTT CAG GTA GTC AAC CAC CAG CAA<br>Asp Val Asn Lys Thr Leu Pro Asn Leu Gln Val Val Asn His Gln Gln<br>            250                  255                  260 | 1152 |
| GGC CCC CAC CAC AGA CAC ATC CTG AAG CTG CTG CCG TCC ATG GAG GCC<br>Gly Pro His His Arg His Ile Leu Lys Leu Leu Pro Ser Met Glu Ala<br>            265                  270                  275 | 1200 |
| ACT GGG GGC GAG AAG TCC AGC ACG CCC ATC AAG GGC CCC AAG AGG GGA<br>Thr Gly Gly Glu Lys Ser Ser Thr Pro Ile Lys Gly Pro Lys Arg Gly<br>280                       285                  290 | 1248 |
| CAT CCT AGA CAG AAC CTA CAC AAG CAT TTT GAC ATC AAT GAG CAT TTG<br>His Pro Arg Gln Asn Leu His Lys His Phe Asp Ile Asn Glu His Leu<br>295                       300                  305                 310 | 1296 |
| CCC TGG ATG ATT GTG CTT TTC CTG CTG CTG GTG CTT GTG GTG ATT GTG<br>Pro Trp Met Ile Val Leu Phe Leu Leu Leu Val Leu Val Val Ile Val<br>                  315                  320                  325 | 1344 |
| GTG TGC AGT ATC CGG AAA AGC TCG AGG ACT CTG AAA AAG GGG CCC CGG<br>Val Cys Ser Ile Arg Lys Ser Ser Arg Thr Leu Lys Lys Gly Pro Arg<br>                  330                  335                  340 | 1392 |
| CAG GAT CCC AGT GCC ATT GTG GAA AAG GCA GGG CTG AAG AAA TCC ATG<br>Gln Asp Pro Ser Ala Ile Val Glu Lys Ala Gly Leu Lys Lys Ser Met<br>            345                  350                  355 | 1440 |
| ACT CCA ACC CAG AAC CGG GAG AAA TGG ATC TAC TAC TGC AAT GGC CAT<br>Thr Pro Thr Gln Asn Arg Glu Lys Trp Ile Tyr Tyr Cys Asn Gly His<br>360                       365                  370 | 1488 |
| GGT ATC GAT ATC CTG AAG CTT GTA GCA GCC CAA GTG GGA AGC CAG TGG<br>Gly Ile Asp Ile Leu Lys Leu Val Ala Ala Gln Val Gly Ser Gln Trp<br>375                       380                  385                 390 | 1536 |
| AAA GAT ATC TAT CAG TTT CTT TGC AAT GCC AGT GAG AGG GAG GTT GCT<br>Lys Asp Ile Tyr Gln Phe Leu Cys Asn Ala Ser Glu Arg Glu Val Ala<br>                  395                  400                  405 | 1584 |
| GCT TTC TCC AAT GGG TAC ACA GCC GAC CAC GAG CGG GCC TAC GCA GCT<br>Ala Phe Ser Asn Gly Tyr Thr Ala Asp His Glu Arg Ala Tyr Ala Ala<br>            410                  415                  420 | 1632 |
| CTG CAG CAC TGG ACC ATC CGG GGC CCC GAG GCC AGC CTC GCC CAG CTA<br>Leu Gln His Trp Thr Ile Arg Gly Pro Glu Ala Ser Leu Ala Gln Leu | 1680 |

```
                425                 430                 435
ATT AGC GCC CTG CGC CAG CAC CGG AGA AAC GAT GTT GTG GAG AAG ATT      1728
Ile Ser Ala Leu Arg Gln His Arg Arg Asn Asp Val Val Glu Lys Ile
        440                 445                 450

CGT GGG CTG ATG GAA GAC ACC ACC CAG CTG GAA ACT GAC AAA CTA GCT      1776
Arg Gly Leu Met Glu Asp Thr Thr Gln Leu Glu Thr Asp Lys Leu Ala
455                 460                 465                 470

CTC CCG ATG AGC CCC AGC CCG CTT AGC CCG AGC CCC ATC CCC AGC CCC      1824
Leu Pro Met Ser Pro Ser Pro Leu Ser Pro Ser Pro Ile Pro Ser Pro
                475                 480                 485

AAC GCG AAA CTT GAG AAT TCC GCT CTC CTG ACG GTG GAG CCT TCC CCA      1872
Asn Ala Lys Leu Glu Asn Ser Ala Leu Leu Thr Val Glu Pro Ser Pro
        490                 495                 500

CAG GAC AAG AAC AAG GGC TTC TTC GTG GAT GAG TCG GAG CCC CTT CTC      1920
Gln Asp Lys Asn Lys Gly Phe Phe Val Asp Glu Ser Glu Pro Leu Leu
            505                 510                 515

CGC TGT GAC TCT ACA TCC AGC GGC TCC TCC GCG CTG AGC AGG AAC GGT      1968
Arg Cys Asp Ser Thr Ser Ser Gly Ser Ser Ala Leu Ser Arg Asn Gly
    520                 525                 530

TCC TTT ATT ACC AAA GAA AAG AAG GAC ACA GTG TTG CGG CAG GTA CGC      2016
Ser Phe Ile Thr Lys Glu Lys Lys Asp Thr Val Leu Arg Gln Val Arg
535                 540                 545                 550

CTG GAC CCC TGT GAC TTG CAG CCT ATC TTT GAT GAC ATG CTC CAC TTT      2064
Leu Asp Pro Cys Asp Leu Gln Pro Ile Phe Asp Asp Met Leu His Phe
                555                 560                 565

CTA AAT CCT GAG GAG CTG CGG GTG ATT GAA GAG ATT CCC CAG GCT GAG      2112
Leu Asn Pro Glu Glu Leu Arg Val Ile Glu Glu Ile Pro Gln Ala Glu
        570                 575                 580

GAC AAA CTA GAC CGG CTA TTC GAA ATT ATT GGA GTC AAG AGC CAG GAA      2160
Asp Lys Leu Asp Arg Leu Phe Glu Ile Ile Gly Val Lys Ser Gln Glu
            585                 590                 595

GCC AGC CAG ACC CTC CTG GAC TCT GTT TAT AGC CAT CTT CCT GAC CTG      2208
Ala Ser Gln Thr Leu Leu Asp Ser Val Tyr Ser His Leu Pro Asp Leu
    600                 605                 610

CTG TAGAACATAG GGATACTGCA TTCTGGAAAT TACTCAATTT AGTGGCAGGG           2261
Leu
615

TGGTTTTTTA ATTTTCTTCT GTTTCTGATT TTTGTTGTTT GGGGTGTGTG TGTGTGTTTG    2321

TGTGTGTGTG TGTGTGTGTG TGTGTGTGTG TGTGTGTGTG TTTAACAGAG AATATGGCCA    2381

GTGCTTGAGT TCTTTCTCCT TCTCTCTCTC TTTTTTTTTT AAATAACTCT TCTGGGAAGT    2441

TGGTTTATAA GCCTTTGCCA GGTGTAACTG TTGTGAAATA CCCACCACTA AAGTTTTTTA    2501

AGTTCCATAT TTTCTCCATT TTGCCTTCTT ATGTATTTTC GAGATTATTC TGTGCACTTT    2561

AAATTTACTT AACTTACCAT AAATGCAGTG TGACTTTTCC CACACACTGG ATTGTGAGGC    2621

TCTTAACTTC TTAAAAGTAT AATGGCATCT TGTGAATCCT ATAAGCAGTC TTTATGTCTC    2681

TTAACATTCA CACCTACTTT TTAAAAACAA ATATTATTAC TATTTTTATT ATTGTTTGTC    2741

CTTTATAAAT TTTCTTAAAG ATTAAGAAAA TTTAAGACCC CATTGAGTTA CTGTAATGCA    2801

ATTCAACTTT GAGTTATCTT TTAAATATGT CTTGTATAGT TCATATTCAT GGCTGAAACT    2861

TGACCACACT ATTGCTGATT GTATGGTTTT CACCTGGACA CCGTGTAGAA TGCTTGATTA    2921

CTTGTACTCT TCTTATGCTA ATATGCTCTG GGCTGGAGAA ATGAAATCCT CAAGCCATCA    2981

GGATTTGCTA TTTAAGTGGC TTGACAACTG GGCCACCAAA GAACTTGAAC TTCACCTTTT    3041

AGGATTTGAG CTGTTCTGGA ACACATTGCT GCACTTTGGA AAGTCAAAAT CAAGTGCCAG    3101

TGGCGCCCTT TCCATAGAGA ATTTGCCCAG CTTTGCTTTA AAAGATGTCT TGTTTTTTAT    3161
```

```
ATACACATAA TCAATAGGTC CAATCTGCTC TCAAGGCCTT GGTCCTGGTG GGATTCCTTC    3221

ACCAATTACT TTAATTAAAA ATGGCTGCAA CTGTAAGAAC CCTTGTCTGA TATATTTGCA    3281

ACTATGCTCC CATTTACAAA TGTACCTTCT AATGCTCAGT TGCCAGGTTC CAATGCAAAG    3341

GTGGCGTGGA CTCCCTTTGT GTGGGTGGGG TTTGTGGGTA GTGGTGAAGG ACCGATATCA    3401

GAAAAATGCC TTCAAGTGTA CTAATTTATT AATAAACATT AGGTGTTTGT TAAAAAAAAA    3461

AAAAAAAAAA AAA                                                      3474
```

(2) INFORMATION FOR SEQ ID NO:2:

(i) SEQUENCE CHARACTERISTICS:
        (A) LENGTH: 655 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Thr Ser Pro Ser Ser Thr Ala Leu Ala Ser Cys Ser Arg
-40             -35                 -30                 -25

Ile Ala Arg Arg Ala Thr Ala Thr Met Ile Ala Gly Ser Leu Leu Leu
            -20                 -15                 -10

Leu Gly Phe Leu Ser Thr Thr Thr Ala Gln Pro Glu Gln Lys Ala Ser
                -5                  1               5

Asn Leu Ile Gly Thr Tyr Arg His Val Asp Arg Ala Thr Gly Gln Val
         10                  15                  20

Leu Thr Cys Asp Lys Cys Pro Ala Gly Thr Tyr Val Ser Glu His Cys
 25                  30                  35                  40

Thr Asn Thr Ser Leu Arg Val Cys Ser Ser Cys Pro Val Gly Thr Phe
                 45                  50                  55

Thr Arg His Glu Asn Gly Ile Glu Lys Cys His Asp Cys Ser Gln Pro
             60                  65                  70

Cys Pro Trp Pro Met Ile Glu Lys Leu Pro Cys Ala Ala Leu Thr Asp
         75                  80                  85

Arg Glu Cys Thr Cys Pro Pro Gly Met Phe Gln Ser Asn Ala Thr Cys
 90                  95                 100

Ala Pro His Thr Val Cys Pro Val Gly Trp Gly Val Arg Lys Lys Gly
105                 110                 115                 120

Thr Glu Thr Glu Asp Val Arg Cys Lys Gln Cys Ala Arg Gly Thr Phe
                125                 130                 135

Ser Asp Val Pro Ser Ser Val Met Lys Cys Lys Ala Tyr Thr Asp Cys
                140                 145                 150

Leu Ser Gln Asn Leu Val Val Ile Lys Pro Gly Thr Lys Glu Thr Asp
        155                 160                 165

Asn Val Cys Gly Thr Leu Pro Ser Phe Ser Ser Thr Ser Pro Ser
        170                 175                 180

Pro Gly Thr Ala Ile Phe Pro Arg Pro Glu His Met Glu Thr His Glu
185                 190                 195                 200

Val Pro Ser Ser Thr Tyr Val Pro Lys Gly Met Asn Ser Thr Glu Ser
                205                 210                 215

Asn Ser Ser Ala Ser Val Arg Pro Lys Val Leu Ser Ser Ile Gln Glu
                220                 225                 230

Gly Thr Val Pro Asp Asn Thr Ser Ser Ala Arg Gly Lys Glu Asp Val
                235                 240                 245
```

```
Asn Lys Thr Leu Pro Asn Leu Gln Val Val Asn His Gln Gln Gly Pro
    250                 255                 260

His His Arg His Ile Leu Lys Leu Leu Pro Ser Met Glu Ala Thr Gly
265                 270                 275                 280

Gly Glu Lys Ser Ser Thr Pro Ile Lys Gly Pro Lys Arg Gly His Pro
                285                 290                 295

Arg Gln Asn Leu His Lys His Phe Asp Ile Asn Glu His Leu Pro Trp
            300                 305                 310

Met Ile Val Leu Phe Leu Leu Val Leu Val Ile Val Val Cys
            315                 320                 325

Ser Ile Arg Lys Ser Ser Arg Thr Leu Lys Lys Gly Pro Arg Gln Asp
    330                 335                 340

Pro Ser Ala Ile Val Glu Lys Ala Gly Leu Lys Lys Ser Met Thr Pro
345                 350                 355                 360

Thr Gln Asn Arg Glu Lys Trp Ile Tyr Tyr Cys Asn Gly His Gly Ile
                365                 370                 375

Asp Ile Leu Lys Leu Val Ala Ala Gln Val Gly Ser Gln Trp Lys Asp
            380                 385                 390

Ile Tyr Gln Phe Leu Cys Asn Ala Ser Glu Arg Glu Val Ala Ala Phe
    395                 400                 405

Ser Asn Gly Tyr Thr Ala Asp His Glu Arg Ala Tyr Ala Ala Leu Gln
410                 415                 420

His Trp Thr Ile Arg Gly Pro Glu Ala Ser Leu Ala Gln Leu Ile Ser
425                 430                 435                 440

Ala Leu Arg Gln His Arg Arg Asn Asp Val Val Glu Lys Ile Arg Gly
                445                 450                 455

Leu Met Glu Asp Thr Thr Gln Leu Glu Thr Asp Lys Leu Ala Leu Pro
            460                 465                 470

Met Ser Pro Ser Pro Leu Ser Pro Ser Pro Ile Pro Ser Pro Asn Ala
    475                 480                 485

Lys Leu Glu Asn Ser Ala Leu Leu Thr Val Glu Pro Ser Pro Gln Asp
490                 495                 500

Lys Asn Lys Gly Phe Phe Val Asp Glu Ser Glu Pro Leu Leu Arg Cys
505                 510                 515                 520

Asp Ser Thr Ser Ser Gly Ser Ser Ala Leu Ser Arg Asn Gly Ser Phe
                525                 530                 535

Ile Thr Lys Glu Lys Lys Asp Thr Val Leu Arg Gln Val Arg Leu Asp
            540                 545                 550

Pro Cys Asp Leu Gln Pro Ile Phe Asp Asp Met Leu His Phe Leu Asn
    555                 560                 565

Pro Glu Glu Leu Arg Val Ile Glu Glu Ile Pro Gln Ala Glu Asp Lys
570                 575                 580

Leu Asp Arg Leu Phe Glu Ile Ile Gly Val Lys Ser Gln Glu Ala Ser
585                 590                 595                 600

Gln Thr Leu Leu Asp Ser Val Tyr Ser His Leu Pro Asp Leu Leu
                605                 610                 615
```

(2) INFORMATION FOR SEQ ID NO:3:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
            35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
                180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Ala Asn Leu Cys Thr Leu Ala Glu Lys Ile
                245                 250                 255

Gln Thr Ile Ile Leu Lys Asp Ile Thr Ser Asp Ser Glu Asn Ser Asn
            260                 265                 270

Phe Arg Asn Glu Ile Gln Ser Leu Val
            275                 280
```

(2) INFORMATION FOR SEQ ID NO:4:

(i) SEQUENCE CHARACTERISTICS:
      (A) LENGTH: 455 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:4:

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
            35                  40                  45
```

-continued

```
Leu Gly Glu Gly Val Ala Gln Pro Cys Gly Ala Asn Gln Thr Val Cys
 50                  55                  60
Glu Pro Cys Leu Asp Ser Val Thr Phe Ser Asp Val Val Ser Ala Thr
 65                  70                  75                  80
Glu Pro Cys Lys Pro Cys Thr Glu Cys Val Gly Leu Gln Ser Met Ser
                 85                  90                  95
Ala Pro Cys Val Glu Ala Asp Asp Ala Val Cys Arg Cys Ala Tyr Gly
            100                 105                 110
Tyr Tyr Gln Asp Glu Thr Thr Gly Arg Cys Glu Ala Cys Arg Val Cys
        115                 120                 125
Glu Ala Gly Ser Gly Leu Val Phe Ser Cys Gln Asp Lys Gln Asn Thr
130                 135                 140
Val Cys Glu Glu Cys Pro Asp Gly Thr Tyr Ser Asp Glu Ala Asn His
145                 150                 155                 160
Val Asp Pro Cys Leu Pro Cys Thr Val Cys Glu Asp Thr Glu Arg Gln
                165                 170                 175
Leu Arg Glu Cys Thr Arg Trp Ala Asp Ala Glu Cys Glu Glu Ile Pro
            180                 185                 190
Gly Arg Trp Ile Thr Arg Ser Thr Pro Pro Glu Gly Ser Asp Ser Thr
        195                 200                 205
Ala Pro Ser Thr Gln Glu Pro Glu Ala Pro Pro Glu Gln Asp Leu Ile
210                 215                 220
Ala Ser Thr Val Ala Gly Val Thr Thr Val Met Gly Ser Ser Gln
225                 230                 235                 240
Pro Val Val Thr Arg Gly Thr Thr Asp Asn Leu Ile Pro Val Tyr Cys
                245                 250                 255
Ser Ile Leu Ala Ala Val Val Val Gly Leu Val Ala Tyr Ile Ala Phe
            260                 265                 270
Lys Arg Trp Asn Ser Cys Lys Gln Asn Lys Gln Gly Ala Asn Ser Arg
        275                 280                 285
Pro Val Asn Gln Thr Pro Pro Pro Glu Gly Glu Lys Leu His Ser Asp
290                 295                 300
Ser Gly Ile Ser Val Asp Ser Gln Ser Leu His Asp Gln Gln Pro His
305                 310                 315                 320
Thr Gln Thr Ala Ser Gly Gln Ala Leu Lys Gly Asp Gly Gly Leu Tyr
                325                 330                 335
Ser Ser Leu Pro Pro Ala Lys Arg Glu Glu Val Glu Lys Leu Leu Asn
            340                 345                 350
Gly Ser Ala Gly Asp Thr Trp Arg His Leu Ala Gly Glu Leu Gly Tyr
        355                 360                 365
Gln Pro Glu His Ile Asp Ser Phe Thr His Glu Ala Cys Pro Val Arg
370                 375                 380
Ala Leu Leu Ala Ser Trp Ala Thr Gln Asp Ser Ala Thr Leu Pro Arg
385                 390                 395                 400
Arg Glu Val Ala Pro Pro Tyr Gln Gly Ala Asp Pro Ile Leu Ala Thr
                405                 410                 415
Ala Leu Ala Ser Asp Pro Ile Pro Asn Pro Leu Gln Lys Trp Glu Asp
            420                 425                 430
Ser Ala His Lys Pro Gln Ser Leu Asp Thr Asp Asp Pro Cys Ser Glu
        435                 440                 445
Ser Thr Ala Thr Ser Pro Val
450                 455
```

(2) INFORMATION FOR SEQ ID NO:5:

(i) SEQUENCE CHARACTERISTICS:
        (A) LENGTH: 455 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Gly Leu Ser Thr Val Pro Asp Leu Leu Pro Leu Val Leu Leu
 1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
                115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Pro Gln Ile Glu Asn Val Lys Gly Thr Glu Asp Ser
                195                 200                 205

Gly Thr Thr Val Leu Leu Pro Leu Val Ile Phe Phe Gly Leu Cys Leu
            210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
                260                 265                 270

Phe Ser Pro Thr Pro Gly Phe Thr Pro Thr Leu Gly Phe Ser Pro Val
                275                 280                 285

Pro Ser Ser Thr Phe Thr Ser Ser Thr Tyr Thr Pro Gly Asp Cys
                290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
```

```
            355                 360                 365
Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
450                 455

(2) INFORMATION FOR SEQ ID NO:6:

(i) SEQUENCE CHARACTERISTICS:
        (A) LENGTH: 365 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCGGCTGTGT ACCCATTGGA GAAAGCAGCA ACCTCCCTCT CACTGGCATT GCAAAGAAAC      60

TGATAGATAT CTTTCCACTG GCTTCCCACT TGGGCTGCTA CAAGCTTCAG GATATCGATA    120

CCATGGCCAT TGCAGTAGTA GATCCATTTT CCCGGTTCTG GGTTGGAGTC ATGGATTTTT    180

CAGCCCTGCC TTTTCCACAA TGGCACTGGG ATCCTGCCGG GGCCCCTTTT TAGAGTCCTC    240

GAGCTTTTCC GGATACTGCA CACCACAATC ACCACAAGCA CCAGCAGCAG GAAAAGCACA    300

ATCATCCAGG GCAAATGCTC ATTGATGTCA AAATGCTTGT GTAGGTTCTG TCTAGGATGT    360

CCCCT                                                                365

(2) INFORMATION FOR SEQ ID NO:7:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGAAACGATG TTGTGGAGAA GATTCGTGGG CTGATGGAAG ACACCACCCA GCTGGAAACT      60

GACAAACTAG CTCTCCCGAT GAGCCCCAGC CCGCTTAGCC CGAGCCCCAT CCCCAGCCCC    120

AACGCGAAAC TTGAGAATTC CGCTCTCCTG ACGGTGGAGC CTTCCCCACA GGACAAGAAC    180

AAGGGCTTCT TCGTGGATGA GTCGGAGCCC CTTCTCCGCT GTACTCTACA TCCAGCGGCT    240

CCTCCGCGCT GAGCAGGAAC GGTTCCTTTA TTACCAAAGA AAAGAAGGAC ACAGTGTTGC    300

GGCAGGTACG CCTGGACCCC TGTAAATTTG CAGCCTATCT TTGATTGACA TGTTCCACTT    360

TCTAAATCCT GAGGAGTT                                                  378

(2) INFORMATION FOR SEQ ID NO:8:

(i) SEQUENCE CHARACTERISTICS:
        (A) LENGTH: 345 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGCAGAGGCA CAAGGTAATT TCTCAATCAT TGGCCATGGG CATGGCTGAC TACAGTCATG      60
GCATTTCTCT ATGCCATTCT CATGCCTGGT AAAGGTCCCC ACAGGGCAAC TGCTGACAGA     120
CGCGCGGCTT GTGTTGGTAC ATGCTCAGAG ACATAGGTTC CTGCTGGACA CTTGTCACAG     180
GTTAGCACCT AGCCGGTGGC ACGGTCAACA TGGCGGTATG TGCCAATGAG ATTCGAGGCC     240
TTCTGTTCTG GCTGAGCTGT GGTGGTGCTA AGGAATCCAA GCGGAGAAGG GAGCCCAGAT     300
CATCGTGGCT GTGGCTGGCG GGCGATGCGG TTCAGGAGGC CGAGG                     345
```

(2) INFORMATION FOR SEQ ID NO:9:

(i) SEQUENCE CHARACTERISTICS:
        (A) LENGTH: 316 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GCTAATTAGC GCCCTGCCAG ACCGGAGAAA CGATGTTTGG AGAAGATTCG TGGGCTGATG      60
GAAGACACCA CCCAGCTGGA AACTGACAAA CTAGCTCTCC CGATGAGCCC CAGCCCGCTT     120
AGCCCGAGCC CCATCCCCAG CCCCAACGCG AAACTTGAGA ATTCCGCTCT CCTGACGGTG     180
GAGCCTTTCC CACAGGACAA GAACAAGGGC TTCTTCGTGG ATGAGTCGGA GCCCCTTCTC     240
CGCTGTACTC TACATCCAGC GGCTCCTCCG GCTGAGCAGG AACGGTTCCT TTATTACCAA     300
GAAAAGAAGG ACACAG                                                     316
```

(2) INFORMATION FOR SEQ ID NO:10:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
AATTCGGCAC GAGGAATCCT ATAAGCAGTC TTTATGTCTC TTAACATTCA CACCTACTTT      60
TTAAAAACAA ATATTATTAC TATTTTTATT ATTGTTTGTC CTTTATAAAT TTTCTTAAAG     120
ATTAAGAAAA TTTAAGACCC CATTGAGTTA CTGTAATGCA ATTCAACTTT GAGTTATCTT     180
TTAAATATGT CTTGTATAGT TCATATTCAT GGCTGAAACT TGACCACACT ATTGCTGATT     240
GTATGGTTCA CCTGGCACCG TGTAGATGCT TGATTACTTG TACTCTCTTA TGTAAATGCT     300
CTGGGCTGGG GAATGAATCC CAGGCTCAGG TTTCCCTATT AAGGGGTTCA CTGGCCCCAA     360
GACTGACTCC CTTGGGGTTG GGTTTGGACA ATGTCTTGGG AGAAAAGCCG GGGCTTCCAG     420
GGTTCCCCTT GTAAGGGTTT TAAAAAAAAG CCATTCTGAG CTCGCCGGGG TCCCATTTAA     480
AAGGGCCCG                                                             489
```

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCCCATGGC TCAGCCAGAA CAGAAG                                              26

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCAAGCTTT TAGGGCAAAT GCTCATTG                                            28

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCCCCGGGG CCATCATGGG GACCTCTCCG AGC                                      33

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGTACCT TAGGGCAAAT GCTCATTG                                            28

(2) INFORMATION FOR SEQ ID NO:15:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGCTCTAGAT CAAGCGTAGT CTGGGACGTC GTATGGGTAG GGCAAATGCT CATTG              55

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO:16:

GGAAGATCTG CCAGAACAGA AGGCCTCGAA T                                    31

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCATCTTCCT GACCTGCTGT AGTCTAGAGC C                                    31

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GCCGACCACG AGCGGGCCTA GTCTAGAGCC                                      30

(2) INFORMATION FOR SEQ ID NO:19:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Thr Cys Asp Lys Cys Pro Ala Gly Thr Tyr Val Ser Glu His Cys Thr
1               5                   10                  15

Asn Thr Ser Leu Arg Val Cys Ser Ser Cys Pro Val Gly Thr Phe Thr
            20                  25                  30

Arg His Glu Asn Gly Ile Glu Lys Cys His Asp Cys Ser Gln Pro Cys
        35                  40                  45

Pro Trp Pro Met Ile Glu Lys Leu Pro Cys Ala Ala Leu Thr Asp Arg
    50                  55                  60

Glu Cys Thr Cys Pro Pro Gly Met Phe Gln Ser Asn Ala Thr Cys Ala
65                  70                  75                  80

Pro His Thr Val Cys Pro Val Gly Trp Gly Val Arg Lys Lys Gly Thr
                85                  90                  95

Glu Thr Glu Asp Val Arg Cys Lys Gln Cys Ala Arg Gly Thr Phe Ser
            100                 105                 110

Asp Val Pro Ser Ser Val Met Pro Cys Lys Ala Tyr Thr Asp Cys Leu
        115                 120                 125

Ser Gln Asn Leu Val Val Ile Lys Pro Gly Thr Lys Glu Thr Asp Asn
    130                 135                 140

Val Cys Gly
```

145

(2) INFORMATION FOR SEQ ID NO:20:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Leu Cys Asp Lys Cys Pro Pro Gly Thr Tyr Leu Lys Gln His Cys Thr
 1               5                  10                  15

Ala Lys Trp Lys Thr Val Cys Ala Pro Cys Pro Asp His Tyr Tyr Thr
            20                  25                  30

Asp Ser Trp His Thr Ser Asp Glu Cys Leu Tyr Cys Ser Pro Val Cys
        35                  40                  45

Lys Glu Leu Gln Tyr Val Lys Gln Glu Cys Asn Arg Thr His Asn Arg
    50                  55                  60

Val Cys Glu Cys Lys Glu Gly Arg Tyr Leu Glu Ile Glu Phe Cys Leu
65                  70                  75                  80

Lys His Arg Ser Cys Pro Pro Gly Phe Gly Val Val Gln Ala Gly Thr
                85                  90                  95

Pro Glu Arg Asn Thr Val Cys Lys Arg Cys Pro Asp Gly Phe Phe Ser
               100                 105                 110

Asn Glu Thr Ser Ser Lys Ala Pro Cys Arg Lys His Thr Asn Cys Ser
               115                 120                 125

Val Phe Gly Leu Leu Leu Thr Gln Lys Gly Asn Ala Thr His Asp Asn
           130                 135                 140

Ile Cys Ser
145
```

(2) INFORMATION FOR SEQ ID NO:21:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Gln Trp Lys Asp Ile Tyr Gln Phe Leu Cys Asn Ala Ser Glu Arg Glu
 1               5                  10                  15

Val Ala Ala Phe Ser Asn Gly Tyr Thr Ala Asp His Glu Arg Ala Tyr
            20                  25                  30

Ala Ala Leu Gln His Trp Thr Ile Arg Gly Pro Glu Ala Ser Leu Ala
            35                  40                  45

Gln Leu Ile Ser Ala Leu Arg Gln His Arg Arg Asn Asp Val Val Glu
    50                  55                  60

Lys Ile Arg
65
```

(2) INFORMATION FOR SEQ ID NO:22:

(i) SEQUENCE CHARACTERISTICS:
        (A) LENGTH: 68 amino acids
        (B) TYPE: amino acid (C) STRANDEDNESS: single
        (D) TOPOLOGY: linear (ii) MOLECULE TYPE: protein (xi) SEQUENCE DESCRIPTION: SEQ ID NO:22:

Gln Val Lys Gly Phe Val Arg Lys Asn Gly Val Asn Glu Ala Lys Ile
1               5                   10                  15

Asp Glu Ile Lys Asn Asp Asn Val Gln Asp Thr Ala Glu Gln Lys Val
            20                  25                  30

Gln Leu Leu Arg Asn Trp His Gln Leu His Gly Lys Lys Glu Ala Tyr
        35                  40                  45

Asp Thr Leu Ile Lys Asp Leu Lys Lys Ala Asn Leu Cys Thr Leu Ala
    50                  55                  60

Glu Lys Ile Gln
65

(2) INFORMATION FOR SEQ ID NO:23:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Arg Trp Lys Glu Phe Val Arg Arg Leu Gly Leu Ser Asp His Glu Ile
1               5                   10                  15

Asp Arg Leu Glu Leu Gln Asn Gly Arg Cys Leu Arg Glu Ala Gln Tyr
            20                  25                  30

Ser Met Leu Ala Thr Trp Arg Arg Thr Arg Arg Glu Ala Thr Leu
        35                  40                  45

Glu Leu Leu Gly Arg Val Leu Arg Asp Met Asp Leu Leu Gly Cys Leu
    50                  55                  60

Glu Asp Ile Glu
65

(2) INFORMATION FOR SEQ ID NO:24:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

Arg Trp Lys Glu Phe Val Arg Thr Leu Gly Leu Arg Glu Ala Glu Ile
1               5                   10                  15

Glu Ala Val Glu Val Glu Ile Gly Arg Phe Arg Asp Gln Gln Tyr Glu
            20                  25                  30

Met Leu Lys Arg Trp Arg Gln Gln Pro Ala Gly Leu Gly Ala Val
        35                  40                  45

Tyr Ala Ala Leu Glu Arg Met Gly Leu Asp Gly Cys Val Glu Asp Leu
    50                  55                  60

Arg
65

-continued (2) INFORMATION FOR SEQ ID NO:25:

(i) SEQUENCE CHARACTERISTICS:
      (A) LENGTH: 67 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:25:

```
Ser Trp Asp Gln Leu Met Arg Gln Leu Asp Leu Thr Lys Asn Glu Ile
1               5                   10                  15

Asp Val Val Arg Ala Gly Thr Ala Gly Pro Gly Asp Ala Leu Tyr Ala
                20                  25                  30

Met Leu Met Lys Trp Val Asn Lys Thr Gly Arg Asn Ala Ser Ile His
            35                  40                  45

Thr Leu Leu Asp Ala Leu Glu Arg Met Glu Glu Arg His Ala Lys Glu
        50                  55                  60

Lys Ile Gln
65
```

(2) INFORMATION FOR SEQ ID NO:26:

(i) SEQUENCE CHARACTERISTICS:
      (A) LENGTH: 67 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:26:

```
Ser Trp Glu Pro Leu Met Arg Lys Leu Gly Leu Met Asp Asn Glu Ile
1               5                   10                  15

Lys Val Ala Lys Ala Glu Ala Ala Gly His Arg Asp Thr Leu Tyr Thr
                20                  25                  30

Met Leu Ile Lys Trp Val Asn Lys Thr Gly Arg Asp Ala Ser Val His
            35                  40                  45

Thr Leu Leu Asp Ala Leu Glu Thr Leu Gly Glu Arg Leu Ala Lys Gln
        50                  55                  60

Lys Ile Glu
65
```